United States Patent
Toone et al.

(10) Patent No.: US 8,907,109 B2
(45) Date of Patent: Dec. 9, 2014

(54) METHODS AND SYSTEMS FOR TREATING CELL PROLIFERATION DISORDERS WITH PSORALEN DERIVATIVES

(71) Applicant: Immunolight, LLC, Detroit, MI (US)

(72) Inventors: Eric Toone, Durham, NC (US); David Gooden, Durham, NC (US); Tuan Vo-Dinh, Chapel Hill, NC (US); Frederic A. Bourke, Jr., Greenwich, CT (US)

(73) Assignees: Immunolight, LLC, Detroit, MI (US); Duke University, Durham, NC (US)

( * ) Notice: Subject to any disclaimer, the term of this patent is extended or adjusted under 35 U.S.C. 154(b) by 0 days.

(21) Appl. No.: 13/739,398

(22) Filed: Jan. 11, 2013

(65) Prior Publication Data

US 2013/0131429 A1    May 23, 2013

Related U.S. Application Data

(62) Division of application No. 12/763,404, filed on Apr. 20, 2010, now Pat. No. 8,383,836.

(60) Provisional application No. 61/171,158, filed on Apr. 21, 2009.

(51) Int. Cl.
C07D 493/00     (2006.01)
C07D 211/92     (2006.01)
(Continued)

(52) U.S. Cl.
CPC .............. *C07D 493/04* (2013.01); *A61K 45/06* (2013.01); *A61N 5/10* (2013.01);
(Continued)

(58) Field of Classification Search
CPC ..................................................... C07D 493/04
USPC ......................................................... 546/347
See application file for complete search history.

(56) References Cited

U.S. PATENT DOCUMENTS 5,587,490 A * 12/1996 Goodrich et al. ............ 549/282

FOREIGN PATENT DOCUMENTS

FR      WO 2001053301        6/2001
WO    WO 0153301     *    7/2001
(Continued)

OTHER PUBLICATIONS

Lartillot et al. Photochemistry and Photobiology (2003), 78(6), 623-632.*

(Continued)

*Primary Examiner* — Nizal Chandrakumar
(74) *Attorney, Agent, or Firm* — Oblon, Spivak, McClelland, Maier & Neustadt, L.L.P.

(57) ABSTRACT

Psoralen compounds of Formula (I):

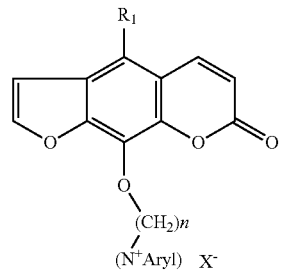

(I)

wherein (N+ Aryl) is a member selected from the group consisting of nitrogen containing aromatic heterocycles of formulae (i)-(iii):

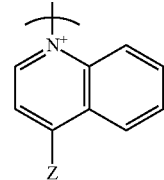

(i)

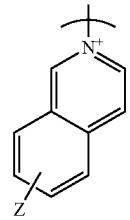

(ii)

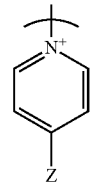

(iii)

wherein Z is a group of formula:

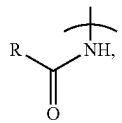

wherein R is $C_1$-$C_{30}$ hydrocarbyl, which may be linear, branched or cyclic and contains from 1 to 15 carbon-carbon double bonds, which may be conjugated or unconjugated with one another or may include an aryl ring, and may contain one or more substituents; $R_1$ is hydrogen, aryl, heteroaryl, alkyl, cycloalkyl, heterocyclyl, alkenyl, alkynyl, alkene-aryl, alkene-heteroaryl, alkene-heterocyclyl, alkene-cycloalkyl, fused cycloalkylaryl, fused cycloalkylheteroaryl, fused heterocyclylaryl, fused heterocyclyheteroaryl, alkylene-fused cycloalkylaryl, alkylene-fused cycloalkylheteroaryl, alkylene-fused heterocyclylaryl, alkylene-fused heterocyclyheteroaryl; n is an integer from 1 to 8 and X is a pharmaceutically acceptable counter ion;
and their use in methods for the treatment of a cell proliferation disorder in a subject, pharmaceutical compositions containing the psoralen derivatives, a kit for performing the method, and a method for causing an autovaccine effect in a subject using the method.

9 Claims, 17 Drawing Sheets

(51) Int. Cl.
*A61K 45/06* (2006.01)
*A61N 5/10* (2006.01)
*A61K 31/453* (2006.01)
*C07D 493/04* (2006.01)
*A61N 5/06* (2006.01)
*A61K 31/4709* (2006.01)
*A61K 41/00* (2006.01)
*A61K 31/4433* (2006.01)

(52) U.S. Cl.
CPC ............ *A61K 31/453* (2013.01); *A61N 5/062* (2013.01); *A61K 31/4709* (2013.01); *A61K 41/0066* (2013.01); *A61K 31/4433* (2013.01)
USPC .......................................... 549/282; 546/347

(56) References Cited

FOREIGN PATENT DOCUMENTS

WO   WO 2006/122222 A2   11/2006
WO   WO 2008/124681 A2   10/2008

OTHER PUBLICATIONS

Venkatesh et al., J. Pharm. Sci. 89, 145-54 (2000) (p. 146, left column).*

Lisa Dalla Via, et al., "Novel Pyrone Side Tetracyclic Psoralen Derivatives: Synthesis and Photobiological Evaluation", J. Med. Chem., 46, American Chemical Society, 2003, pp. 3800-3810.

Adriana Chilin, et al., "Coumarin as Attractive Casein Kinase 2 (CK2) Inhibitor Scaffold: An Integrate Approach to Elucidate the Putative Binding Motif and Explain Structure-Activity Relationships", J. Med. Chem., 51, American Chemical Society, 2008, pp. 752-759.

Via et al. Journal of Medicinal Chemistry, 2003, 46, 3800-3810.

U.S. Appl. No. 13/739,414, filed Jan. 11, 2013, Toone, et al.

U.S. Appl. No. 14/256,550, filed Apr. 18, 2014, Bourke, et al.

* cited by examiner

METHODS AND SYSTEMS FOR TREATING CELL PROLIFERATION DISORDERS WITH PSORALEN DERIVATIVES

CROSS REFERENCE TO RELATED APPLICATIONS

This application is a divisional of U.S. patent application Ser. No. 12/763,404, filed Apr. 20, 2010, the entire contents of which is hereby incorporated by reference. This application is related to U.S. patent application Ser. No. 11/935,655, filed Nov. 6, 2007, U.S. Provisional application Ser. Nos. 60/910,663, filed Apr. 8, 2007 and 61/030,437, filed Feb. 21, 2008, and U.S. patent application Ser. No. 12/389,946, filed Feb. 20, 2009, the contents of each of which is hereby incorporated herein by reference. This application is also related to and claims priority to U.S. provisional application 61/171,158, filed Apr. 21, 2009, the entire contents of which are hereby incorporated herein by reference.

BACKGROUND OF THE INVENTION

1. Field of Invention

The present invention relates to methods and systems for treating cell proliferation disorders using derivatives of psoralen, that provide better distinction between normal, healthy cells and those cells suffering a cell proliferation disorder (hereafter "target cells") and preferably that can be performed using non-invasive or minimally invasive techniques.

2. Discussion of the Background

Cell Proliferation Disorders

There are several types of cell proliferation disorders. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Of these, cancer is perhaps the most well known. The term "cancer" generally refers to a diverse class of diseases that are commonly characterized by an abnormal proliferation of the diseased cells. A unifying thread in all known types of cancer is the acquisition of abnormalities in the genetic material of the cancer cell and its progeny. Once a cell becomes cancerous, it will proliferate without respect to normal limits, invading and destroying adjacent tissues, and may even spread to distant anatomic sites through a process called metastasis. These life-threatening, malignant properties of cancers differentiate them from benign tumors, which are self-limited in their growth and do not invade or metastasize.

The impact of cancer on society cannot be overstated. The disease may affect people at all ages, with a risk factor that significantly increases with a person's age. It has been one of the principal causes of death in developed countries and, as our population continues to age, it is expected to be an even greater threat to our society and economy. Therefore, finding cures and effective treatments for cancer has been, and remains, a priority within the biomedical research community.

Treatment Methods

Existing treatments for cell proliferation disorders such as cancer include surgery, chemotherapy, radiation therapy, immunotherapy, monoclonal antibody therapy, and several other lesser known methods. The choice of therapy usually depends on the location and severity of the disorder, the stage of the disease, as well as the patient's response to the treatment.

While some treatments may only seek to manage and alleviate symptoms of the disorder, the ultimate goal of any effective therapy is the complete removal or cure of all disordered cells without damage to the rest of the body. With cancer, although surgery may sometimes accomplish this goal, the propensity of cancer cells to invade adjacent tissue or to spread to distant sites by microscopic metastasis often limits the effectiveness of this option. Similarly, the effectiveness of current chemotherapy is often limited by toxicity to other tissues in the body. Radiation therapy suffers from similar shortcomings as other aforementioned treatment methods. Most of these cancer treatment methods, including radiation therapy, are known to cause damage to DNA, which if not repaired during a critical stage in mitosis, the splitting of the cell during cell proliferation, leads to a programmed cell death, i.e. apoptosis. Further, radiation tends to damage healthy cells, as well as malignant tumor cells.

A number of patents describe ex vivo treatment of bodily fluids, for example blood. Blood is obtained from a patient, treated with a photosensitive agent, exposed to UV radiation, and reinjected to the patient (i.e. extracorporeal photopheresis). Alternatively, a patient can be treated in vivo with a photosensitive agent followed by the withdrawal of a sample from the patient, treatment with UV radiation in vitro (ex vivo), and reinjecting the patient with the treated sample. This method is known for producing an autovaccine. A method of treating a patient with a photosensitive agent, exposing the patient to an energy source and generating an autovaccine effect wherein all steps are conducted in vivo has not been described. See WO 03/049801, U.S. Pat. No. 6,569,467; U.S. Pat. No. 6,204,058; U.S. Pat. No. 5,980,954; U.S. Pat. No. 6,669,965; U.S. Pat. No. 4,838,852; U.S. Pat. No. 7,045,124, and U.S. Pat. No. 6,849,058. Moreover, the side effects of extracorporeal photopheresis are well known and include nausea, vomiting, cutaneous erythema, hypersensitivity to sunlight, and secondary hematologic malignancy. Researchers are attempting to use photopheresis in experimental treatments for patients with cardiac, pulmonary and renal allograft rejection; autoimmune diseases, and ulcerative colitis.

A survey of known treatment methods reveals that these methods tend to face a primary difficulty of differentiating between normal cells and target cells when delivering treatment, often due to the production of singlet oxygen which is known to be non-selective in its attack of cells, as well as the need to perform the processes ex vivo, or through highly invasive procedures, such as surgical procedures in order to reach tissues more than a few centimeters deep within the subject.

U.S. Pat. No. 5,829,448 describes simultaneous two photon excitation of photo-agents using irradiation with low energy photons such as infrared or near infrared light (NRI). A single photon and simultaneous two photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation. However, the use of NRI or UV radiation is known to penetrate tissue to only a depth of a few centimeters. Thus any treatment deep within the subject would necessarily require the use of ex vivo methods or highly invasive techniques to allow the irradiation source to reach the tissue of interest.

Chen et al., J. Nanosci. and Nanotech., 6:1159-1166 (2006); Kim et al., JACS, 129:2669-2675 (2007); U.S. 2002/

0127224; and U.S. Pat. No. 4,979,935 each describe methods for treatment using various types of energy activation of agents within a subject. However, each suffers from the drawback that the treatment is dependent on the production of singlet oxygen to produce the desired effect on the tissue being treated, and is thus largely indiscriminate in affecting both healthy cells and the diseased tissue desired to be treated.

U.S. Pat. No. 6,908,591 discloses methods for sterilizing tissue with irradiation to reduce the level of one or more active biological contaminants or pathogens, such as viruses, bacteria, yeasts, molds, fungi, spores, prions or similar agents responsible, alone or in combination, for transmissible spongiform encephalopathies and/or single or multicellular parasites, such that the tissue may subsequently be used in transplantation to replace diseased and/or otherwise defective tissue in an animal. The method may include the use of a sensitizer such as psoralen, a psoralen-derivative or other photosensitizer in order to improve the effectiveness of the irradiation or to reduce the exposure necessary to sterilize the tissue. However, the method is not suitable for treating a patient and does not teach any mechanisms for stimulating the photosensitizers, indirectly.

U.S. Pat. No. 6,235,508 discloses antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photo sensitizer, inactivating substantially all of the contaminants in the blood, without destroying the red blood cells. The blocking agent prevents or reduces deleterious side reactions of the photosensitizer, which would occur if not in the presence of the blocking agent. The mode of action of the blocking agent is not predominantly in the quenching of any reactive oxygen species, according to the reference.

Also, U.S. Pat. No. 6,235,508 suggests that halogenated photosensitizers and blocking agents might be suitable for replacing 8-methoxypsoralen (8-MOP) in photophoresis and in treatment of certain proliferative cancers, especially solid localized tumors accessible via a fiber optic light device or superficial skin cancers. However, the reference fails to address any specific molecules for use in treating lymphomas or any other cancer. Instead, the reference suggests a process of photophoresis for antiviral treatments of raw blood and plasma.

U.S. Pat. No. 6,235,508 teaches away from 8-MOP and 4'-aminomethyl-4,5',8-trimethylpsoralen (AMT) and many other photoactivatable molecules, which are taught to have certain disadvantages. Fluorescing photosensitizers are said to be preferred, but the reference does not teach how to select a system of fluorescent stimulation or photoactivation using fluorescent photosensitizers. Instead, the fluorescing photosensitizer is limited to the intercalator that is binding to the DNA. The reference suggests that fluorescence indicates that such an intercalator is less likely to stimulate oxygen radicals. Thus, the reference fails to disclose any mechanism of photoactivation of an intercalator other than by direct photoactivation by UV light, although use of a UV light probe or X-rays is suggested for penetrating deeper into tissues. No examples are provided for the use of a UV light probe or for use of X-rays. No example of any stimulation by X-ray radiation is taught.

Psoralens and Related Compounds

U.S. Pat. No. 6,235,508 further teaches that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The crosslinking reaction appears to be specific for a thymine (DNA) or a uracil (RNA) base. Binding proceeds only if psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

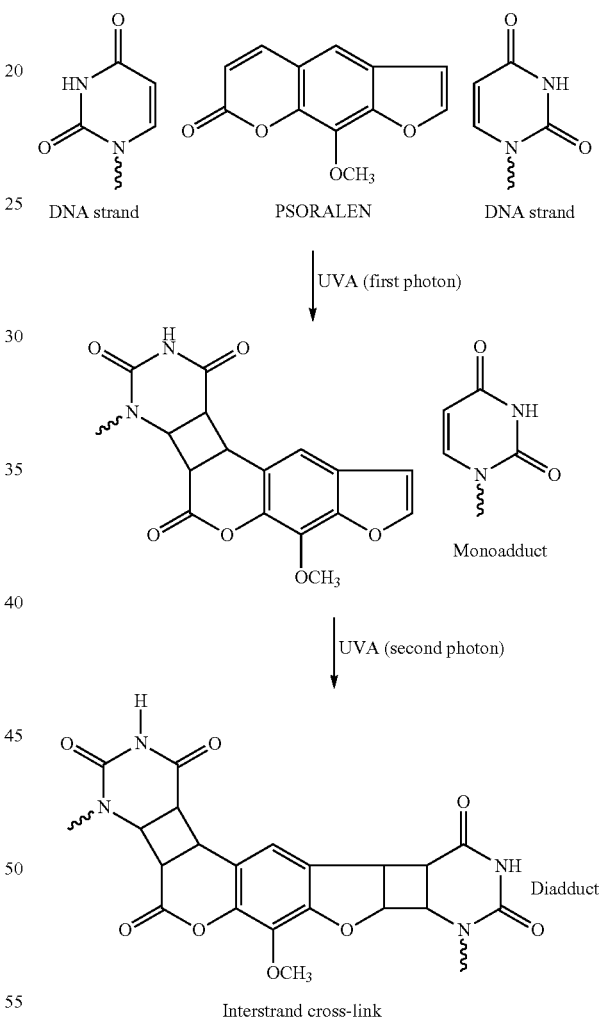

In addition, the reference teaches that 8-MOP is unsuitable for use as an antiviral, because it damages both cells and viruses. Lethal damage to a cell or virus occurs when the psoralen is intercalated into a nucleic acid duplex in sites containing two thymines (or uracils) on opposing strands but only when it sequentially absorbs 2 UVA photons and thymines (or uracils) are present. U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens. Regardless, it is believed that no auto vaccine effect has been observed.

The best known photoactivatable compounds are derivatives of psoralen or coumarin, which are nucleic acid intercalators. The use of psoralen and coumarin photosensitizers can give rise to alternative chemical pathways for dissipation of the excited state that are either not beneficial to the goal of viral inactivation, or that are actually detrimental to the process. For psoralens and coumarins, this chemical pathway is likely to lead to the formation of a variety of ring-opened species, such as shown below for coumarin:

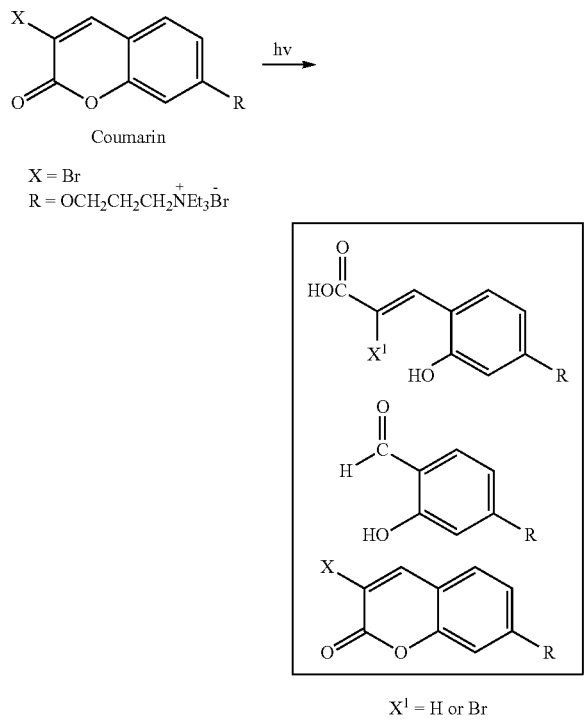

Coumarin $X = Br$
$R = OCH_2CH_2CH_2NEt_3^+Br^-$ $X^1 = H$ or $Br$

Research in this field over-simplifies mechanisms involved in the photoactivating mechanism and formation of highly reactive oxygen species, such as singlet oxygen. Both may lead to inactivating damage of tumor cells, viruses and healthy cells. However, neither, alone or combined, lead to an auto vaccine effect. This requires an activation of the body's own immune system to identify a malignant cell or virus as threat and to create an immune response capable of lasting cytotoxic effects directed to that threat. It is believed, without being limiting in any way, that photoactivation and the resulting apoptosis of malignant cells that occurs in extracorporeal photophoresis causes the activation of an immune response with cytotoxic effects on untreated malignant cells. While the complexity of the immune response and cytotoxid effects is fully appreciated by researchers, a therapy that harnesses the system to successfully stimulate an auto vaccine effect against a targeted, malignant cell has been elusive, except for extracorporeal photophoresis for treating lymphoma.

Midden (W. R. Midden, Psoralen DNA photobiology, Vol I1 (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes. U.S. Pat. No. 6,235,508 teaches that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 of Heindel discloses a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference.

U.S. Pat. No. 5,984,887 discloses using extracorporeal photophoresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

Photodynamic Therapy (PDT)

Photodynamic therapy (PDT) is a treatment modality that uses a photosensitizing agent and laser light to kill cells. PDT retains several photosensitizers in tumors for a longer time than in normal tissues, thus offering potential improvement in treatment selectivity. See corner C., "Determination of [3H]- and [14C] hematoporphyrin derivative distribution in malignant and normal tissue," Cancer Res 1979, 3 9: 146-15 1; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favourable selectivity," Br J Cancer 1986, 54:717-725. Photodynamic therapy uses light of a specific wavelength to activate the photosensitizing agent. Various light sources have been developed for PDT that include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photo sensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently.

Furthermore, when laser light is administered via external illumination of tissue surfaces, the treatment effect of PDT is confined to a few millimeters (i.e. superficial). The reason for this superficial limitation is mainly the limited penetration of the visible light used to activate the photosensitizer. Thus, PDT is used to treat the surfaces of critical organs, such as lungs or intra-abdominal organs, without damage to the to underlying structures. However, even these treatments require significantly invasive techniques to treat the surface of the affected organs. Clinical situations use the procedure in conjunction with surgical debulking to destroy remnants of microscopic or minimal gross disease. It is possible that the laser light and small amount of remaining microscopic and minimal gross disease results in too little or highly damaged structures. Pre-clinical data show that some immune response is generated, but clinical trials have reported no auto vaccine effect similar to that produced by extracorporeal photophoresis in clinical conditions. Instead, immune response appears to be vigorous only under limited conditions and only for a limited duration.

Psoralen has been shown to have some activity against wild-type cancer lines in extracorporeal treatments, such as photodynamic therapy (PDT). However, many cancer lines are p53 mutant strains, which are more resistant to psoralen in treatments.

Problems

It is well recognized that a major problem associated with the existing methods of diagnosis and treatment of cell proliferation disorders is in differentiation of normal cells from target cells. Such target specificity is difficult to achieve by way of surgery since the strategy there is simply to cut out a large enough portion of the affected area to include all diseased cells and hope that no diseased cells have spread to other distant locations.

With chemotherapy, while some degree of differentiation can be achieved, healthy cells are generally adversely affected by chemo-agents. As in surgery, the treatment strategy in chemotherapy is also to kill off a large population of cells, with the understanding that there are far more normal cells than diseased cells so that the organism can recover from the chemical assault.

Radiation therapy works by irradiating cells with high levels of high energy radiation such as high energy photon, electron, or proton. These high energy beams ionize the atoms which make up a DNA chain, which in turn leads to cell death. Unlike surgery, radiation therapy does not require placing patients under anesthesia and has the ability to treat tumors deep inside the body with minimal invasion of the body. However, the high doses of radiation needed for such therapies damages healthy cells just as effectively as it does diseased cells. Thus, similar to surgery, differentiation between healthy and diseased cells in radiation therapy is only by way of location. There is no intrinsic means for a radiation beam to differentiate between a healthy cell from a diseased cell either.

Other methods may be more refined. For example, one form of advanced treatment for lymphoma known as extracorporeal photopheresis involves drawing the patient's blood from his body into an instrument where the white cells (buffy coat) are separated from the plasma and the red blood cells. A small amount of the plasma separated in this process is then isolated and mixed with a photosensitizer (PS), a drug that can be activated by light. The buffy coat is then exposed to a light to activate the drug. The treated blood is then returned to the patient. In this example, one may think of the target-specificity problem as being solved by separating the blood from the rest of the body where the target components are easily exposed.

However, this procedure has its drawbacks; it requires drawing blood from the patient, thus requiring cumbersome machinery to perform and may require blood transfusion in order to maintain the volume of blood flow in the machine. Further, this also limits the size of the patient that can be treated, since the extracorporeal volume is great and too much withdrawal of blood increases the risk of hypovolemic shock. The method is also limited to treating blood-born cell proliferation related disorders such as lymphoma, and is not capable of treating solid tumors or other types of non-blood related cell proliferation disorders.

A problem encountered in PDT therapy is the inability to treat target areas that are more than a few centimeters beneath the surface of the skin without significant invasive techniques, and the fact that PDT typically operates by generation of sufficient quantities of singlet oxygen to cause cell lysis. However, singlet oxygen in sufficient concentration will lyse not only target cells, but also healthy cells rather indiscriminately.

Therefore, there still exists a need for better and more effective treatments that can more precisely target the diseased cells without causing substantial side-effects or collateral damages to healthy tissues, and which are capable of treating even solid tumors or other types of non-blood related cell proliferation disorders. Additionally, while psoralen has been shown to have some activity against wild-type cancer lines in certain treatments, such as extracorporeal photopheresis and photodynamic therapy (PDT), many cancer lines are p53 mutant strains, which are more resistant to psoralen in treatments.

Accordingly, there is a need for derivatives of psoralen that can be used in such treatments for both wild-type and p53 mutant cancer cells.

SUMMARY OF THE INVENTION

Accordingly, one object of the present invention is to provide a derivatives of psoralen that can be used in treatment of cell proliferation disorders, particularly in treatment of cancers that are p53 mutants.

A further object of the present invention is to provide a method for the treatment of a cell proliferation disorder using the psoralen derivatives that permits treatment of a subject in any area of the body while being non-invasive and having high selectivity for targeted cells relative to healthy cells.

A further object of the present invention is to provide a method for treatment of a cell proliferation disorder using the psoralen derivatives which can use any suitable energy source as the initiation energy source to activate the psoralen derivative and thereby cause a predetermined cellular change to treat cells suffering from a cell proliferation disorder.

A further object of the present invention is to provide a method for treatment of a cell proliferation disorder using an energy cascade to activate the psoralen derivative that then treats cells suffering from a cell proliferation disorder.

A further object of the present invention is to provide a method for using the psoralen derivative to generate an auto-vaccine effect in a subject, which can be in vivo thus avoiding the need for ex vivo treatment of subject tissues or cells, or can be ex vivo.

A further object of the present invention is to provide a computer implemented system for performing the methods of the present invention.

A still further object of the present invention is to provide a kit and a pharmaceutical composition for use in the present invention methods.

These and other objects of the present invention, which will become more apparent in conjunction with the following detailed description of the preferred embodiments, either alone or in combinations thereof, have been satisfied by the discovery of A psoralen compound of Formula (I):

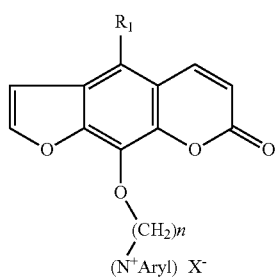

(I)

wherein (N⁺ Aryl) is a member selected from the group consisting of nitrogen containing aromatic heterocycles of formulae (i)-(iii):

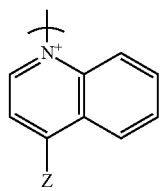

(i)

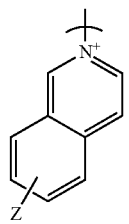

(ii)

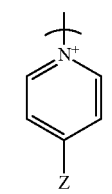

(iii)

wherein Z is a group of formula:

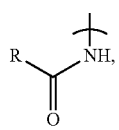

wherein R is $C_1$-$C_{30}$ hydrocarbyl, which may be linear, branched or cyclic and contains from 1 to 15 carbon-carbon double bonds, which may be conjugated or unconjugated with one another or may include an aryl ring, and may contain one or more substituents; $R_1$ is hydrogen, aryl, heteroaryl, alkyl, cycloalkyl, heterocyclyl, alkenyl, alkynyl, alkene-aryl, alkene-heteroaryl, alkene-heterocyclyl, alkene-cycloalkyl, fused cycloalkylaryl, fused cycloalkylheteroaryl, fused heterocyclylaryl, fused heterocyclyheteroaryl, alkylene-fused cycloalkylaryl, alkylene-fused cycloalkylheteroaryl, alkylene-fused heterocyclylaryl, alkylene-fused heterocyclyheteroaryl; n is an integer from 1 to 8 and X is a pharmaceutically acceptable counter ion;

and their use in methods for the treatment of a cell proliferation disorder in a subject, pharmaceutical compositions containing the psoralen derivatives, a kit for performing the method, and a method for causing an autovaccine effect in a subject using the method.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
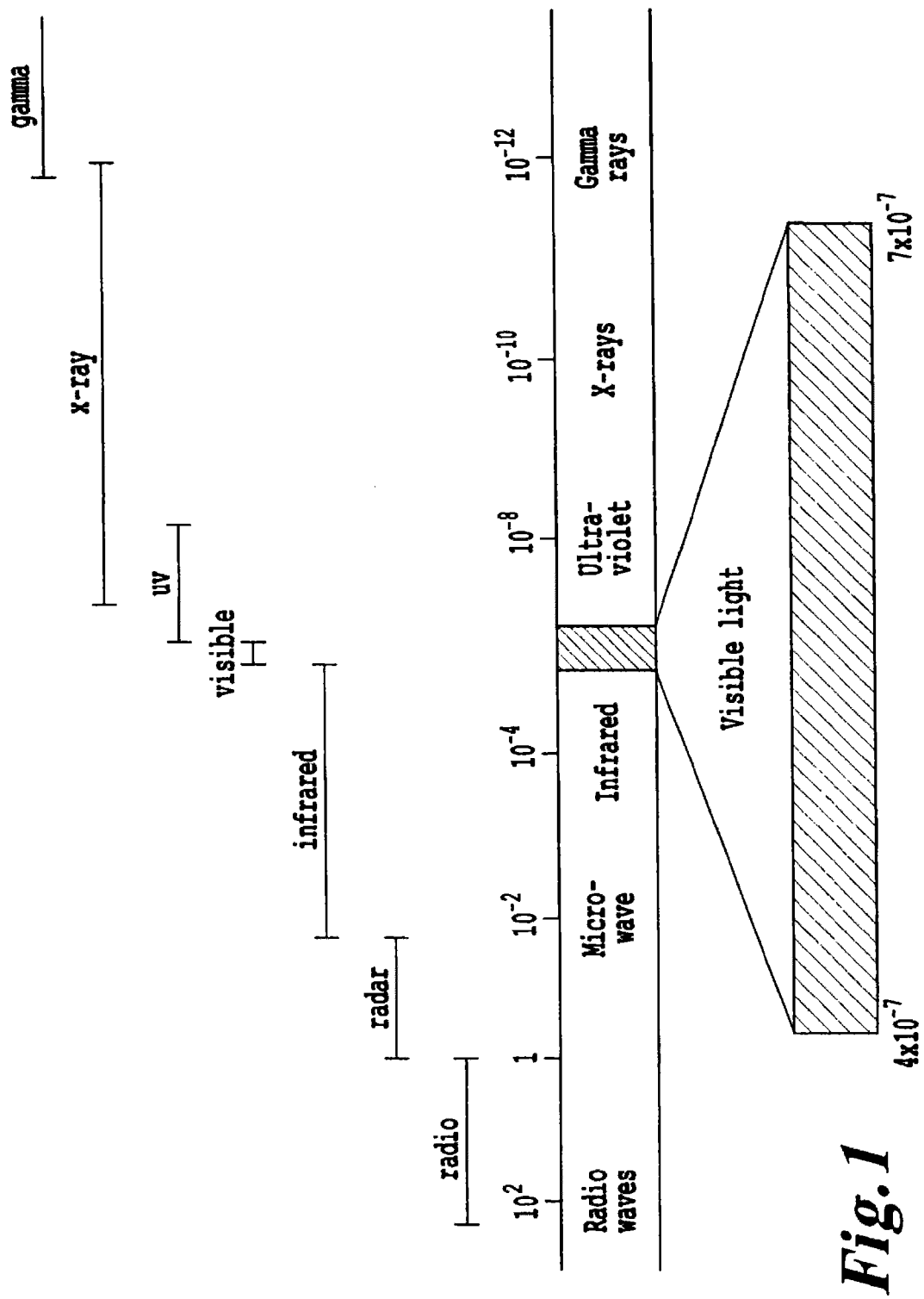
FIG. 1 provides an exemplary electromagnetic spectrum in meters (1 nm equals meters).

The present invention sets forth a novel method of treating cell proliferation disorders that is effective, specific, and has few side-effects. Those cells suffering from a cell proliferation disorder are referred to herein as the target cells. A treatment for cell proliferation disorders, including solid tumors, is capable of chemically binding cellular nucleic acids, including but not limited to, the DNA or mitochondrial DNA or RNA of the target cells. For example, in the present invention a psoralen derivative is exposed in situ to an energy source capable of activating the psoralen derivative.

The psoralen derivatives of the present invention have the following general Formula (I):

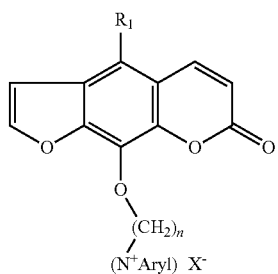
(I)

Wherein (N⁺ Aryl) is a member selected from the group consisting of nitrogen containing aromatic heterocycles of formulae (i)-(iii):

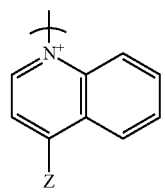
(i)

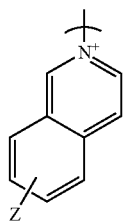
(ii)

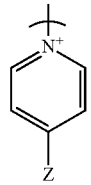
(iii)

Wherein Z is a group of formula:

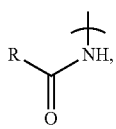

wherein R is $C_1$-$C_{30}$ hydrocarbyl, which may be linear, branched or cyclic and contains from 1 to 15 carbon-carbon double bonds, which may be conjugated or unconjugated with one another or may include an aryl ring, and may contain one or more substituents; $R_1$ is hydrogen, aryl, heteroaryl, alkyl, cycloalkyl, heterocyclyl, alkenyl, alkynyl, alkene-aryl, alkene-heteroaryl, alkene-heterocyclyl, alkene-cycloalkyl, fused cycloalkylaryl, fused cycloalkylheteroaryl, fused heterocyclylaryl, fused heterocyclylheteroaryl, alkylene-fused cycloalkylaryl, alkylene-fused cycloalkylheteroaryl, alkylene-fused heterocyclylaryl, alkylene-fused heterocyclylheteroaryl; n is an integer from 1 to 8 and X is a pharmaceutically acceptable counter ion. X preferably includes, but is not limited to, halides, benzoate, citrate, fumarate, maleate, mesylate, nitrate, phosphate, sulfate, or tartrate.

Most preferred psoralen derivatives in the present invention are compounds (1)-(2) and (5)-(16) in the following table:

| | psoralen derivative |
|---|---|
| 1 | |

-continued
| | psoralen derivative |
|---|---|
| 2 | 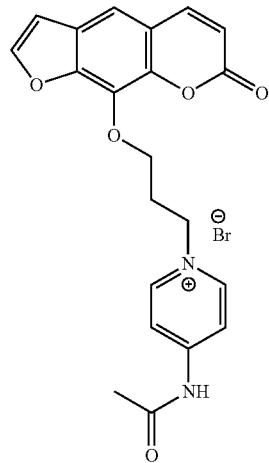 [SMILES: CC(=O)Nc1cc[n+](CCCOc2c3occc3cc3ccc(=O)oc23)cc1 ; [Br-]] |
| 5 | 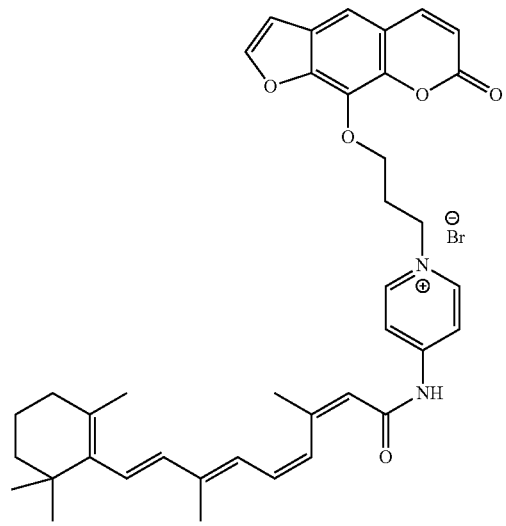 [SMILES: CC1=C(/C=C/C(C)=C/C=C\C(C)=C/C(=O)Nc2cc[n+](CCCOc3c4occc4cc4ccc(=O)oc34)cc2)C(C)(C)CCC1 ; [Br-]] |
| 6 | 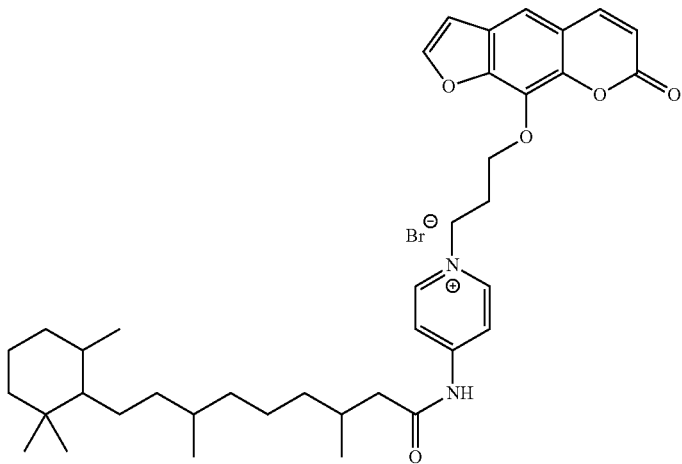 [SMILES: CC(CCCC(C)CC(=O)Nc1cc[n+](CCCOc2c3occc3cc3ccc(=O)oc23)cc1)CCC1C(C)CCCC1(C)C ; [Br-]] |

| | psoralen derivative |
|---|---|
| 7 | 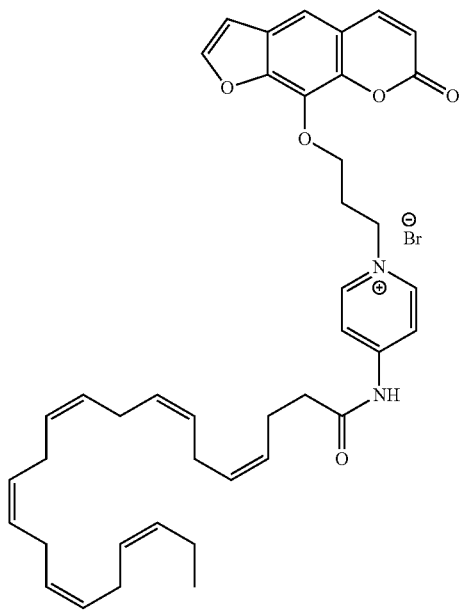 [SMILES: CC/C=C\C/C=C\C/C=C\C/C=C\C/C=C\C/C=C\CCC(=O)Nc1cc[n+](CCCOc2c3occc3cc3ccc(=O)oc23)cc1 ; [Br-]] |
| 8 | 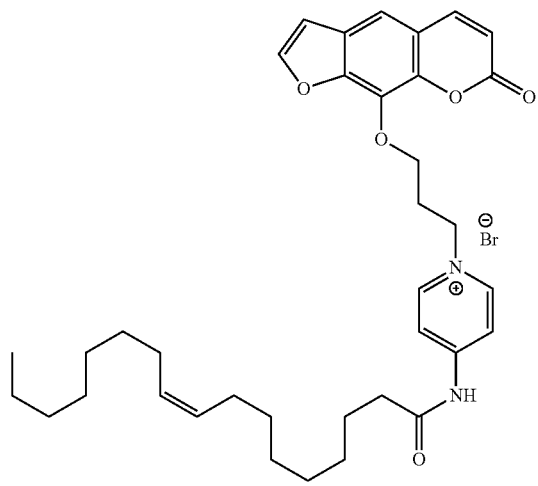 [SMILES: CCCCCCC/C=C\CCCCCCCC(=O)Nc1cc[n+](CCCOc2c3occc3cc3ccc(=O)oc23)cc1 ; [Br-]] |
| 9 | 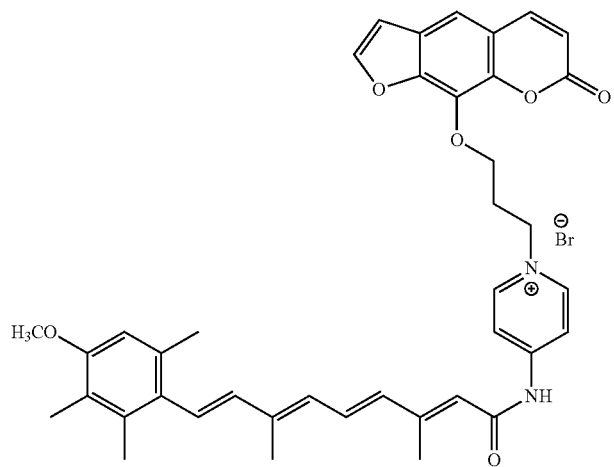 [SMILES: COc1cc(C)c(/C=C/C(C)=C/C=C/C(C)=C/C(=O)Nc2cc[n+](CCCOc3c4occc4cc4ccc(=O)oc34)cc2)c(C)c1C ; [Br-]] |

| | psoralen derivative |
|---|---|
| 10 | 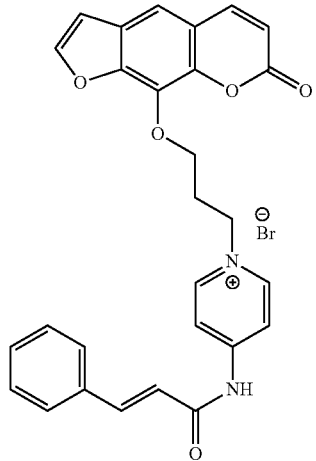 [SMILES: O=C(/C=C/c1ccccc1)Nc1cc[n+](CCCOc2c3occc3cc3ccc(=O)oc23)cc1 ; [Br-]] |
| 11 | 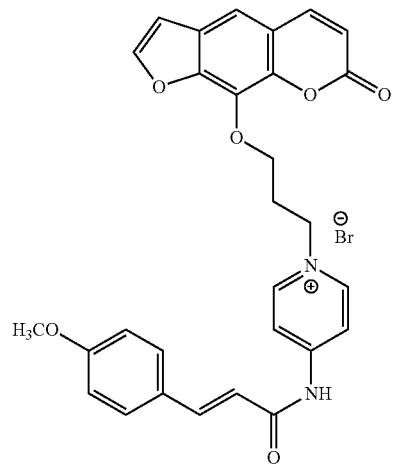 [SMILES: COc1ccc(/C=C/C(=O)Nc2cc[n+](CCCOc3c4occc4cc4ccc(=O)oc34)cc2)cc1 ; [Br-]] |
| 12 | 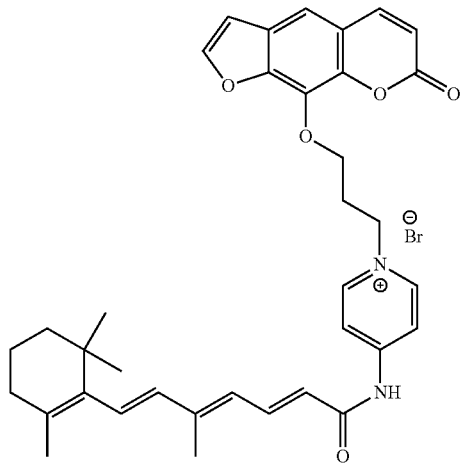 [SMILES: CC1=C(/C=C/C(C)=C/C=C/C(=O)Nc2cc[n+](CCCOc3c4occc4cc4ccc(=O)oc34)cc2)C(C)(C)CCC1 ; [Br-]] |

-continued
| | psoralen derivative |
|---|---|
| 13 | 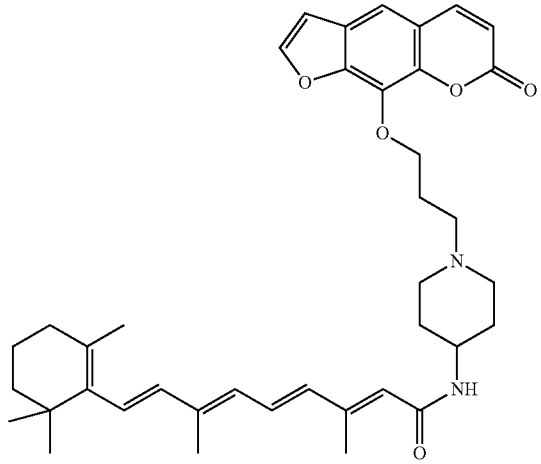 [SMILES: CC1=C(/C=C/C(C)=C/C=C/C(C)=C/C(=O)NC2CCN(CCCOc3c4occc4cc4ccc(=O)oc34)CC2)C(C)(C)CCC1] |
| 14 | 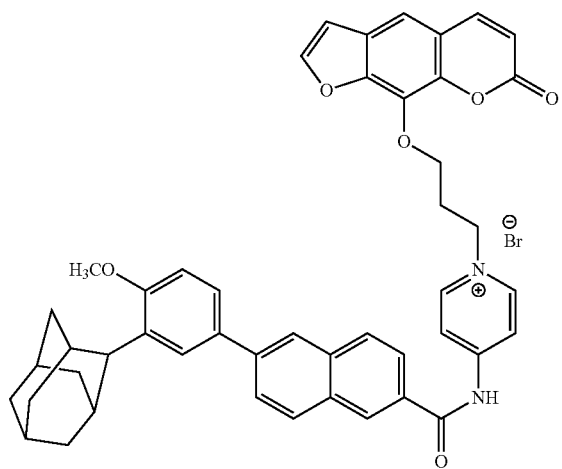 [SMILES: COc1ccc(-c2ccc3cc(C(=O)Nc4cc[n+](CCCOc5c6occc6cc6ccc(=O)oc56)cc4)ccc3c2)cc1C1C2CC3CC(C2)CC1C3 ; [Br-]] |
| 15 | 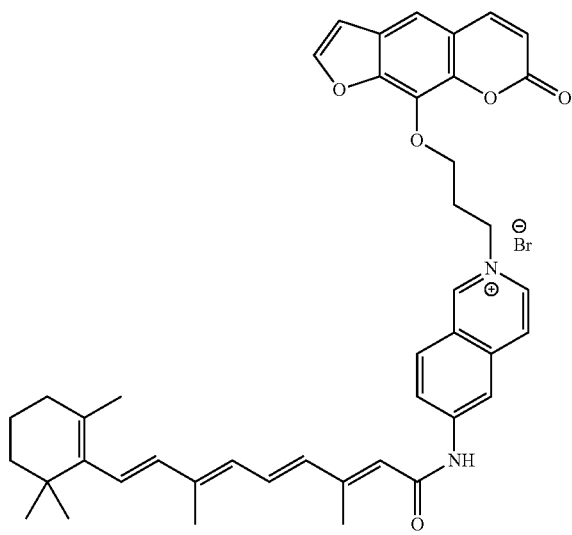 [SMILES: CC1=C(/C=C/C(C)=C/C=C/C(C)=C/C(=O)Nc2ccc3c[n+](CCCOc4c5occc5cc5ccc(=O)oc45)ccc3c2)C(C)(C)CCC1 ; [Br-]] |

| psoralen derivative |
|---|
| 16 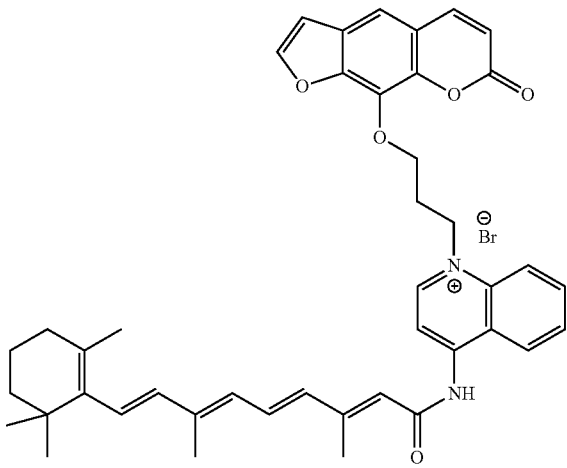 [SMILES: CC1=C(/C=C/C(C)=C/C=C/C(C)=C/C(=O)Nc2cc[n+](CCCOc3c4occc4cc4ccc(=O)oc34)c3ccccc23)C(C)(C)CCC1 ; [Br-]] |

As noted above, an object of the present invention is to treat cell proliferation disorders. Exemplary cell proliferation disorders may include, but are not limited to, cancer, as well as bacterial and viral infections where the invading bacteria grows at a much more rapid rate than cells of the infected host. In addition, treatment for certain developmental stage diseases related to cell proliferation, such as syndactyl), are also contemplated.

Accordingly, in one embodiment, the present invention provides methods that are capable of overcoming the shortcomings of the existing methods. In general, a method in accordance with the present invention utilizes the principle of energy transfer to and among molecular agents to control delivery and activation of pharmaceutically active agents such that delivery of the desired pharmacological effect is more focused, precise, and effective than the conventional techniques.

Generally, the present invention provides methods for the treatment of cell proliferation disorders, in which an initiation energy source provides an initiation energy that activates an activatable pharmaceutical agent to treat target cells within the subject. In one preferred embodiment, the initiation energy source is applied indirectly to the activatable pharmaceutical agent, preferably in proximity to the target cells. Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the activatable pharmaceutical agent within a subject. In one embodiment, the initiation energy interacts with a previously administered energy modulation agent which then activates the activatable pharmaceutical agent. In another embodiment, the initiation energy itself activates the activatable pharmaceutical agent. In either embodiment, the initiation energy source cannot be within line-of-sight of the activatable pharmaceutical agent. By "cannot be within line-of-sight" is meant that if a hypothetical observer were located at the location of the activatable pharmaceutical agent, that observer would be unable to see the source of the initiation energy.

Although not intending to be bound by any particular theory or be otherwise limited in any way, the following theoretical discussion of scientific principles and definitions are provided to help the reader gain an understanding and appreciation of the present invention.

As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the present invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

FIG. 1 provides an exemplary electromagnetic spectrum in meters (1 nm equals meters).

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, or a combination thereof.

As used herein, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy. In preferred embodiments, the energy modulation agent receives higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence. Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as a lipid, chitin or chitin-derivative, a chelate or other functionalized carrier that is capable of concentrating the UV-A emitting source in a specific target tumor.

Additionally, the energy modulation agent can be used alone or as a series of two or more energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Although the psoralen derivative and the energy modulation agent can be distinct and separate, it will be understood that the two need not be independent and separate entities. In fact, the two may be associated with each other via a number of different configurations. Where the psoralen derivative and energy modulation agent are independent and separately movable from each other, they generally interact with each other via diffusion and chance encounters within a common surrounding medium. Where they are not separate, they may be combined into one single entity.

The initiation energy source can be any energy source capable of providing energy at a level sufficient to activate the activatable agent directly, or to provide the energy modulation agent with the input needed to emit the activation energy for the psoralen derivative (indirect activation). Preferable initiation energy sources include, but are not limited to, UV-A lamps or fiber optic lines, a light needle, an endoscope, and a linear accelerator that generates x-ray, gamma-ray, or electron beams. In a preferred embodiment the initiation energy capable of penetrating completely through the subject. Within the context of the present invention, the phrase "capable of penetrating completely through the subject" is used to refer to energy that can penetrate to any depth within the subject to activate the psoralen derivative. It is not required that the any of the energy applied actually pass completely through the subject, merely that it be capable of doing so in order to permit penetration to any desired depth to activate the psoralen derivative. Exemplary initiation energy sources that are capable of penetrating completely through the subject include, but are not limited to, x-rays, gamma rays, electron beams, microwaves and radio waves.

In one embodiment, the source of the initiation energy can be a radiowave emitting nanotube, such as those described by K. Jensen, J. Weldon, H. Garcia, and A. Zettl in the Department of Physics at the University of California at Berkeley (see http://socrates.berkeley.edu/~argon/nanoradio/radio.html, the entire contents of which are hereby incorporated by reference). These nanotubes can be administered to the subject, and preferably would be coupled to the activatable pharmaceutical agent or the energy modulation agent, or both, such that upon application of the initiation energy, the nanotubes would accept the initiation energy (prefereably radiowaves), then emit radiowaves in close proximity to the activatable pharmaceutical agent, or in close proximity to the energy modulation agent, to then cause activation of the activatable pharmaceutical agent. In such an embodiment, the nanotubes would act essentially as a radiowave focusing or amplification device in close proximity to the activatable pharmaceutical agent or energy modulation agent.

Alternatively, the energy emitting source may be an energy modulation agent that emits energy in a form suitable for absorption by the transfer agent. For example, the initiation energy source may be acoustic energy and one energy modulation agent may be capable of receiving acoustic energy and emitting photonic energy (e.g. sonoluminescent molecules) to be received by another energy modulation agent that is capable of receiving photonic energy. Other examples include transfer agents that receive energy at x-ray wavelength and emit energy at UV wavelength, preferably at UV-A wavelength. As noted above, a plurality of such energy modulation agents may be used to form a cascade to transfer energy from initiation energy source via a series of energy modulation agents to activate the activatable agent.

Signal transduction schemes as a drug delivery vehicle may be advantageously developed by careful modeling of the cascade events coupled with metabolic pathway knowledge to sequentially or simultaneously activate multiple activatable pharmaceutical agents to achieve multiple-point alterations in cellular function.

In a preferred embodiment, the psoralen derivative, upon activation, binds to DNA or RNA or other structures in a cell. The activated energy state of the psoralen derivative is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the present invention administers a psoralen derivative to a patient, stimulates the psoralen derivative to induce cell damage, and generates an auto vaccine effect. In one further preferred embodiment, the psoralen derivative is stimulated via a resonance energy transfer.

One advantage is that multiple wavelengths of emitted radiation may be used to selectively stimulate one or more psoralen derivatives or energy modulation agents capable of stimulating the one or more psoralen derivatives. The energy modulation agent is preferably stimulated at a wavelength and energy that causes little or no damage to healthy cells, with the energy from one or more energy modulation agents being transferred, such as by Foerster Resonance Energy Transfer, to the psoralen derivative that damages the cell and causes the onset of the desired cellular change, such as apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

Alternatively, one can administer the initiation energy source to the subject. Within the context of the present invention, the administering of the initiation energy source means the administration of an agent, that itself produces the initiation energy, in a manner that permits the agent to arrive at the target cell within the subject without being surgically inserted into the subject. The administration can take any form, including, but not limited to, oral, intravenous, intraperitoneal, inhalation, etc. Further, the initiation energy source in this embodiment can be in any form, including, but not limited to, tablet, powder, liquid solution, liquid suspension, liquid dispersion, gas or vapor, etc. In this embodiment, the initiation energy source includes, but is not limited to, chemical energy sources, nanoemitters, nanochips, and other nanomachines that produce and emit energy of a desired frequency. Recent advances in nanotechnology have provided examples of various devices that are nanoscale and produce or emit energy, such as the Molecular Switch (or Mol-Switch) work by Dr. Keith Firman of the EC Research and Development Project, or the work of Cornell et al. (1997) who describe the construction of nanomachines based around ion-channel switches only 1.5 nm in size, which use ion channels formed in an artificial membrane by two gramicidin molecules: one in the lower layer of the membrane attached to a gold electrode and one in the upper layer tethered to biological receptors such as antibodies or nucleotides. When the receptor captures a target molecule or cell, the ion channel is broken, its conductivity drops, and the biochemical signal is converted into an electrical signal. These nanodevices could also be coupled with the present invention to provide targeting of the target cell, to deliver the initiation energy source directly at the desired site. In another embodiment, the present invention includes the administration of the psoralen derivative, along with administration of a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the subject or inside the subject, with the chemiluminescence, phosphorescence or bioluminescence being allowed to activate the psoralen derivative in vivo after administration. The administration of the psoralen derivative and the source of chemical energy can be performed sequentially in any order or can be performed simultaneously. In the case of certain sources of such chemical energy, the administration of the chemical energy source can be performed after activation outside the subject, with the lifetime of the emission of the energy being up to several hours for certain types of phosphorescent materials for example. There are no known previous efforts to use resonance energy transfer of any kind to activate an intercalator to bind DNA.

Yet another example is that nanoparticles or nanoclusters of certain atoms may be introduced such that are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a cell are capable of stimulating activation of photoactivatable agents disposed in a distant portion of the cell, so long as the distance does not greatly exceed $R_0$. As examples of energy modulation agents, gold nanospheres having a size of 5 atoms of gold have been shown to have an emission band in the ultraviolet range, recently. Additionally, nanoparticles of compounds such as $Y_2O_3$ or CdS are known as X-ray scintillation materials, generating UV radiation upon exposure to X-rays. The emitted UV radiation can be used to activate the psoralen derivatives of the present invention.

The present invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the psoralen derivative.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to activated psoralen derivatives, provided that such activated psoralens degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Alternatively, the psoralen derivative may be exposed to an excitation energy source implanted in a tumor. The psoralen derivative may be directed to a receptor site by a carrier having a strong affinity for the receptor site. Within the context of the present invention, a "strong affinity" is preferably an affinity having an equilibrium dissociation constant, $K_j$, at least in the nanomolar, nM, range or higher. Preferably, the carrier may be a polypeptide and may form a covalent bond with a photoactive agent, for example. The polypeptide may be an insulin, interleukin, thymopoietin or transferrin, for example. Alternatively, a psoralen derivative may have a strong affinity for the target cell without binding to a carrier.

A receptor site may be any of the following: nucleic acids of nucleated blood cells, molecule receptor sites of nucleated blood cells, the antigenic sites on nucleated blood cells, epitopes, or other sites where psoralen derivatives are capable of destroying a targeted cell.

In one embodiment, thin fiber optic lines are inserted in the tumor and laser light is used to photoactivate the psoralen derivative. In another embodiment, a plurality of sources for supplying electromagnetic radiation energy or energy transfer are provided by one or more molecules administered to a patient. The molecules may emit stimulating radiation in the correct band of wavelength to stimulate the psoralen derivative, or the molecules may transfer energy by a resonance energy transfer or other mechanism directly to the psoralen derivative or indirectly by a cascade effect via other molecular interactions.

In another embodiment, the patient's own cells are removed and genetically modified to provide photonic emissions. For example, tumor or healthy cells may be removed, genetically modified to induce bioluminescence and may be reinserted at the site of the tumor to be treated. The modified, bioluminescent cells may be further modified to prevent further division of the cells or division of the cells only so long as a regulating agent is present. Administration of an intercalator, systemically or targeting tumor cells, that is capable of photoactivation by bioluminescent cells may produce conditions suitable for creating an auto vaccine effect due to apoptosis of malignant cells. Preferably, apoptosis triggers and stimulates the body to develop an immune response targeting the malignant cells.

In an additional embodiment, the psoralen derivative of the present invention can be used in conventional PDT or extracorporeal photopheresis treatments to provide an ex vivo treatment of cancer, preferably treatment of a cancer that is a p53 mutant strain.

In a further embodiment, a biocompatible emitting source, such as a fluorescing metal or metal oxide nanoparticle or fluorescing dye molecule, is selected that emits in the UV-A band. The UV-A emitting source is directed to the site of a tumor. The UV-A emitting source may be directed to the site of the tumor by systemically administering the UV-A emitting source. Preferably, the UV-A emitting source is concentrated in the tumor site, such as by physical insertion or by conjugating the UV-A emitting molecule with a tumor specific carrier, such as a lipid, chitin or chitin-derivative, a chelate or other functionalized carrier that is capable of concentrating the UV-A emitting source in a specific target tumor, as is known in the art.

In another embodiment, a Stokes shift of an emitting source or a series of emitting sources arranged in a cascade is selected to convert a shorter wavelength energy, such as X-rays, to a longer wavelength fluorescence emission such a optical or UV-A, which is used to stimulate a psoralen derivative at the location of the tumor cells. Preferably, the psoralen derivative is selected to cause an apoptosis sequence in tumor cells without causing substantial harm to normal, healthy cells. More preferably, the apoptosis sequence then leads to an auto vaccine effect that targets the malignant tumor cells throughout the patient's body.

In a further embodiment, some of the tumor cells are treated in vitro using a UV-A source to stimulate the psoralen derivative. Apoptosis of the tumor cells is monitored, and some or all of the fragments and remnants of the apoptosis process are reintroduced into the site of a tumor. Preferably, the portion of fragments, cellular structures and remnants are selected such that an auto vaccine effect is generated that leads to further apoptosis of tumor cells without substantially harming healthy tissues, causing solid tumors to shrink.

Figure 2A:
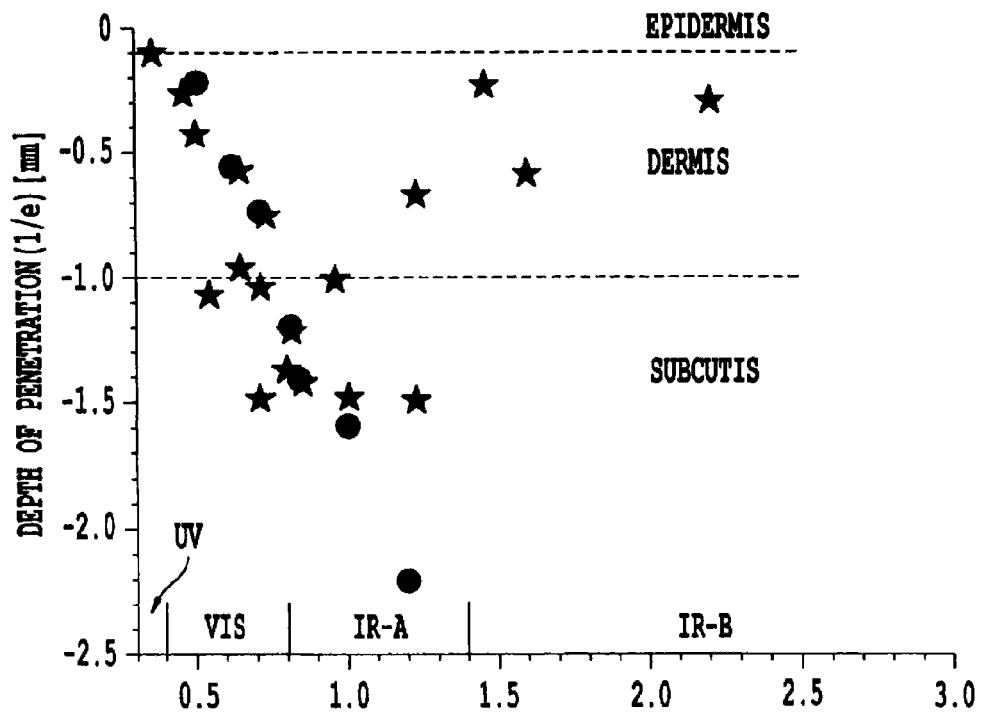
FIG. 2A and FIG. 2B are graphical representations of the depth of penetration of various wavelengths of energy into living tissue.
Figure 2B:
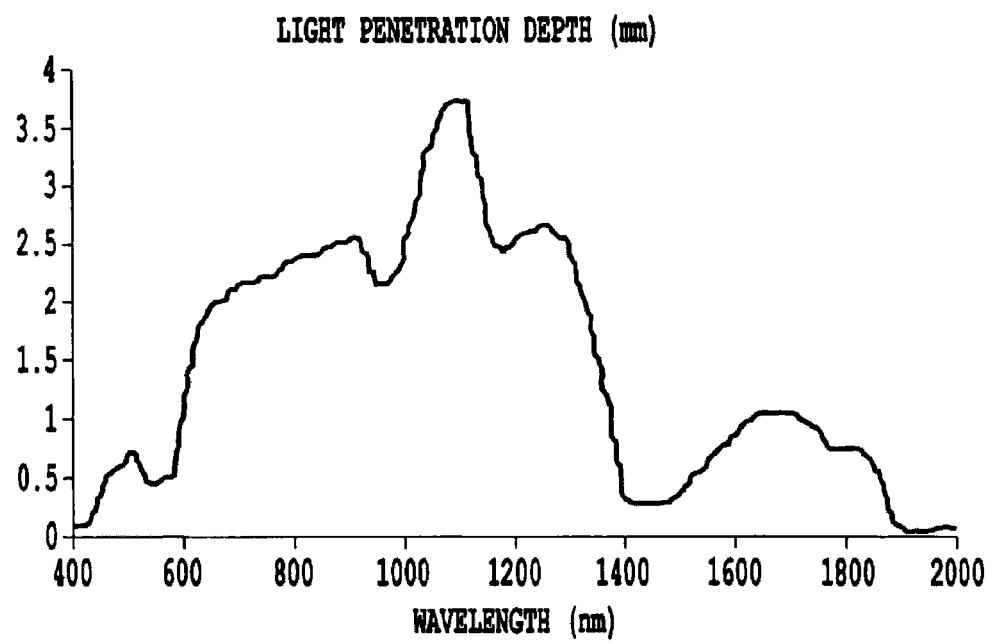

The energy source can be any desired source capable of activating the psoralen derivative, either directly or indirectly. Suitable energy sources include, but are not limited to, those described in U.S. application Ser. No. 11/935,655, filed Nov. 6, 2007, incorporated herein by reference. FIGS. 2A and 2B show the penetration depth of various wavelengths of light in the UV to IR range (FIG. 2A) or from 400-2000 nm (FIG. 2B). Thus in order to penetrate to depths greater than that indicated in these figures and activate the psoralen compound of the present invention, it would be necessary to use an invasive method of applying the energy (through an incision in the subject) or to use a non-invasive energy source capable of penetrating through the subject to a depth sufficient to reach the target area, which can then be converted using an energy modulation agent to the desired frequency to activate the psoralen compound.

In another embodiment, one can use a plasmonics active agent to enhance or modify the applied energy (or in cases where an energy modulation agent is present the energy emitted from the energy modulation agent) for activating the psoralen compounds. Suitable plasmonics active agents have been described in U.S. application Ser. No. 12/417,779, filed Apr. 3, 2009; U.S. application Ser. No. 12/389,946, filed Feb. 20, 2009; U.S. Provisional Application 61/030,437, filed Feb. 21, 2008; and U.S. Provisional Application 61/042,561, filed Apr. 4, 2008; the contents of each of which are hereby incorporated by reference. These plasmonics active agents can be used singly or in combinations of two or more, and can be used with or without the presence of energy modulation agents. Further, the energy modulation agents can be used with or without the presence of plasmonics active agents.

In general, the approach may be used with any source for the excitation of higher electronic energy states, such as electrical, chemical and/or radiation, individually or combined into a system for activating an activatable molecule. The process may be a photopheresis process or may be similar to photopheresis. While photopheresis is generally thought to be limited to photonic excitation, such as by UV-light, other forms of radiation may be used as a part of a system to activate an activatable molecule. Radiation includes ionizing radiation which is high energy radiation, such as an X-ray or a gamma ray, which interacts to produce ion pairs in matter. Radiation also includes high linear energy transfer irradiation, low linear energy transfer irradiation, alpha rays, beta rays, neutron beams, accelerated electron beams, and ultraviolet rays. Radiation also includes proton, photon and fission-spectrum neutrons. Higher energy ionizing radiation may be combined with chemical processes to produce energy states favorable for resonance energy transfer, for example. Other combinations and variations of these sources of excitation energy may be combined as is known in the art, in order to stimulate the activation of the psoralen derivative. In one example, ionizing radiation is directed at a solid tumor and stimulates, directly or indirectly, activation of the psoralen derivative, as well as directly damaging the DNA of malignant tumor cells. In this example, either the effect of ionizing radiation or the photophoresis-like activation of the psoralen derivative may be thought of as an adjuvant therapy to the other.

In one embodiment, the present invention provides a method for treating a cell proliferation disorder in a subject, comprising:

(1) administering to the subject a psoralen derivative of the present invention that is capable of effecting a predetermined cellular change when activated; and (2) applying an initiation energy from an initiation energy source to the subject, activating the psoralen derivative in situ, thus causing the predetermined cellular change to occur, wherein occurrence of the predetermined cellular change causes an increase in rate or decrease in rate of cell proliferation to treat the cell proliferation disorder.

In a further embodiment, the present invention provides a method for treating a cell proliferation disorder in a subject, comprising:

(1) administering to the subject one or more energy modulation agents and a psoralen derivative of the present invention that is capable of effecting a predetermined cellular change when activated; and (2) applying an initiation energy from an initiation energy source to the subject, wherein the one or more energy modulation agents convert the initiation energy applied to UV-A or visible energy, which then activates the psoralen derivative in situ, thus causing the predetermined cellular change to occur, wherein occurrence of the predetermined cellular change causes an increase in rate or decrease in rate of cell proliferation to treat the cell proliferation disorder.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. However, in the present invention, it is most preferable to avoid production of an amount of singlet oxygen that would cause cell lysis, due to its indiscriminate nature of attack, lysing both target cells and healthy cells. Accordingly, it is most preferred in the present invention that the level of singlet oxygen production caused by the initiation energy used or psoralen derivative upon activation be less than the level needed to cause cell lysis.

In yet another embodiment, the psoralen derivative, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin, albumin or transferrin, for example. Alternatively, the psoralen derivative may have a strong affinity for the target cell without binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the present invention.

In another example, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death even if exposed to photoactivated agents that cause apoptosis, provided that such photoactivated agents degenerate from the excited state to a lower energy state prior to binding, mitosis or other mechanisms for creating damage to the cells of a substantial fraction of the healthy stem cells. To further protect healthy cells from the effect of photoactivatable agents, blocking agents that block uptake of the photoactivatable agents, prior to their activation, may be administered.

U.S. Pat. No. 6,235,508, discloses that a variety of blocking agents have been found to be suitable for this purpose, some of which are traditional antioxidants, and some of which are not. Suitable blocking agents include, but are not limited to, histidine, cysteine, tryrosine, tryptophan, ascorbate, N-acetyl cysteine, propyl gallate, mercaptopropionyl glycine, butylated hydroxytoluene (BHT) and butylated hydroxyanisole (BHA).

In a further embodiment, methods in accordance with the present invention may further include adding an additive to alleviate treatment side-effects. Exemplary additives may include, but are not limited to, antioxidants, adjuvant, or combinations thereof. In one exemplary embodiment, a psoralen derivative of the present invention is used as the activatable pharmaceutical agent, UV-A is used as the activating energy, and antioxidants are added to reduce the unwanted side-effects of irradiation.

The psoralen derivative as well as the energy modulation agent, can be incorporated into pharmaceutical compositions suitable for administration. Such compositions typically comprise the psoralen derivative and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic to dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the psoralen derivative is prepared with a carrier that will protect the psoralen derivative against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Methods of administering agents according to the present invention are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection.

Such transfected cells may be inserted or otherwise targeted at the site where diseased cells are located. In this embodiment, the initiation energy source may be a biochemical source as such ATP, in which case the initiation energy source is considered to be directly implanted in the transfected cell. Alternatively, a conventional micro-emitter device capable of acting as an initiation energy source may be transplanted at the site of the diseased cells.

It will also be understood that the order of administering the different agents is not particularly limited. Thus in some embodiments the activatable pharmaceutical agent may be administered before the energy modulation agent, while in other embodiments the energy modulation agent may be administered prior to the psoralen derivative. It will be appreciated that different combinations of ordering may be advantageously employed depending on factors such as the absorption rate of the agents, the localization and molecular trafficking properties of the agents, and other pharmacokinetics or pharmacodynamics considerations.

An advantage of the methods of the present invention is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system.

In another aspect, the present invention also provides methods for producing an autovaccine, including: (1) providing a population of targeted cells; (2) treating the cells ex vivo with a psoralen derivative of Formula (I); (3) activating the psoralen derivative with a UV-A source to induce apoptosis in the targeted cells; and (4) returning the apoptic cells back to the host to induce an autovaccine effect against the targeted cell, wherein the apoptic cells cause an autovaccine effect.

A further embodiment is the use of the present invention for the treatment of skin cancer. In this example, the psoralen derivative is given to the patient, and is delivered to the skin lesion via the blood supply. An activation source having limited penetration ability (such as UV or IR) is shined directly on the skin—in the case of the present psoralen derivatives, it would preferably be a UV light, or an IR source. With the use of an IR source, the irradiation would penetrate deeper and generate UV via two single photon events with the psoralen derivative.

In a further embodiment, methods according to this aspect of the present invention further include a step of separating the components of apoptic cells into fractions and testing each fraction for autovaccine effect in a host. The components thus isolated and identified may then serve as an effective autovaccine to stimulate the host's immune system to suppress growth of the targeted cells.

The present invention methods can be used alone or in combination with other therapies for treatment of cell proliferation disorders. Additionally, the present invention methods can be used, if desired, in conjunction with recent advances in chronomedicine, such as that detailed in Giacchetti et al, *Journal of Clinical Oncology*, Vol 24, No 22 (August 1), 2006: pp. 3562-3569. In chronomedicine it has been found that cells suffering from certain types of disorders, such as cancer, respond better at certain times of the day than at others. Thus, chronomedicine could be used in conjunction with the present methods in order to augment the effect of the treatments of the present invention.

In another aspect, the present invention further provides systems and kits for practicing the above described methods.

In one embodiment, a system in accordance with the present invention may include: (1) an initiation energy source; (2) one or more energy modulation agents; and (3) one or more psoralen derivatives of Formula (I).

In another embodiment, a system in accordance with the present invention may include an initiation energy source and one or more psoralen derivatives, and optionally one or more energy modulation agents and/or one or more plasmonics active agents as disclosed in U.S. application Ser. No. 12/389,946, filed Feburary 20, 2009, already incorporated by reference above.

Figure 3:
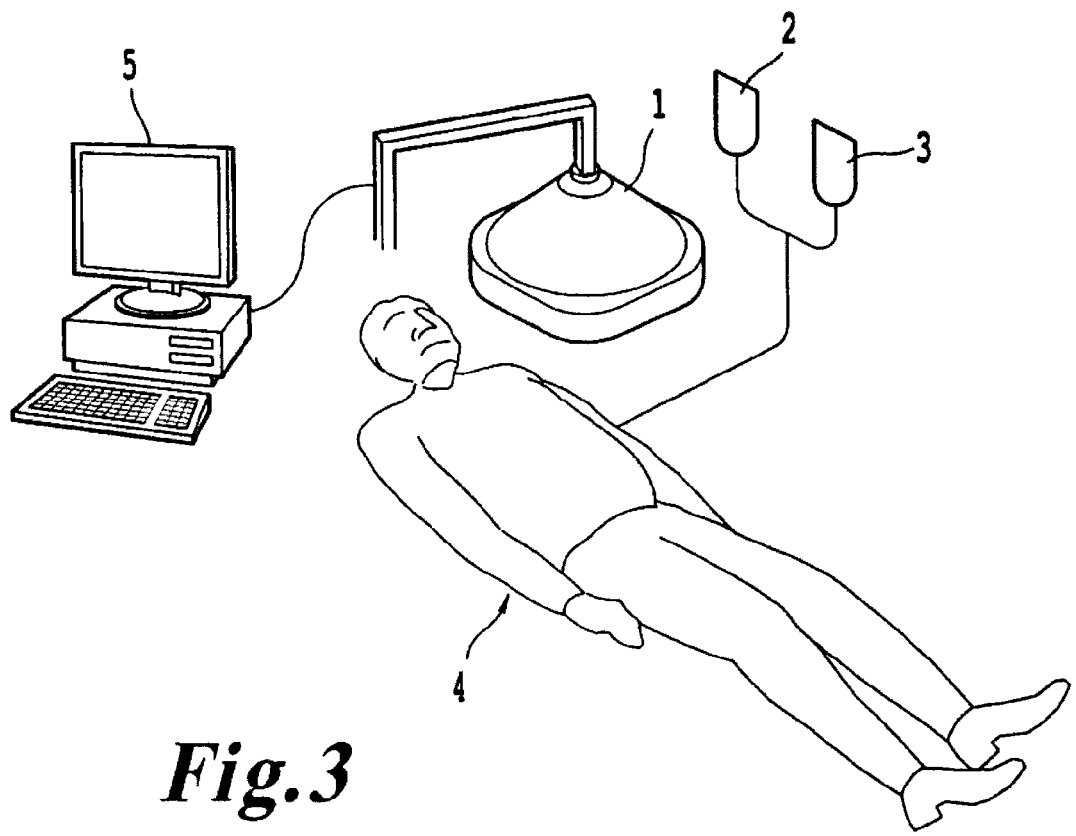
FIG. 3 illustrates a system according to one exemplary embodiment of the present invention.
Figure 4:
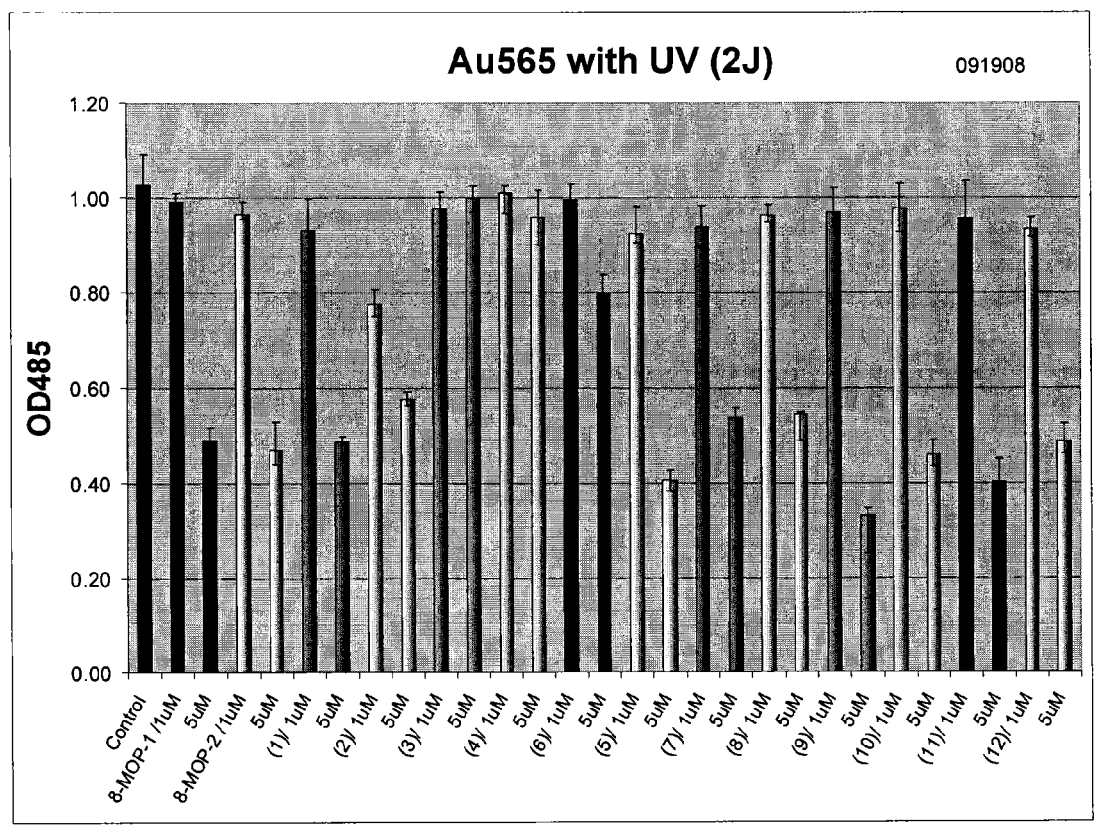
FIG. 4 provides an antenna plot of cell proliferation assay data using various compounds of the present invention with Au565 cancer cells and UV irradiation.
Figure 5:
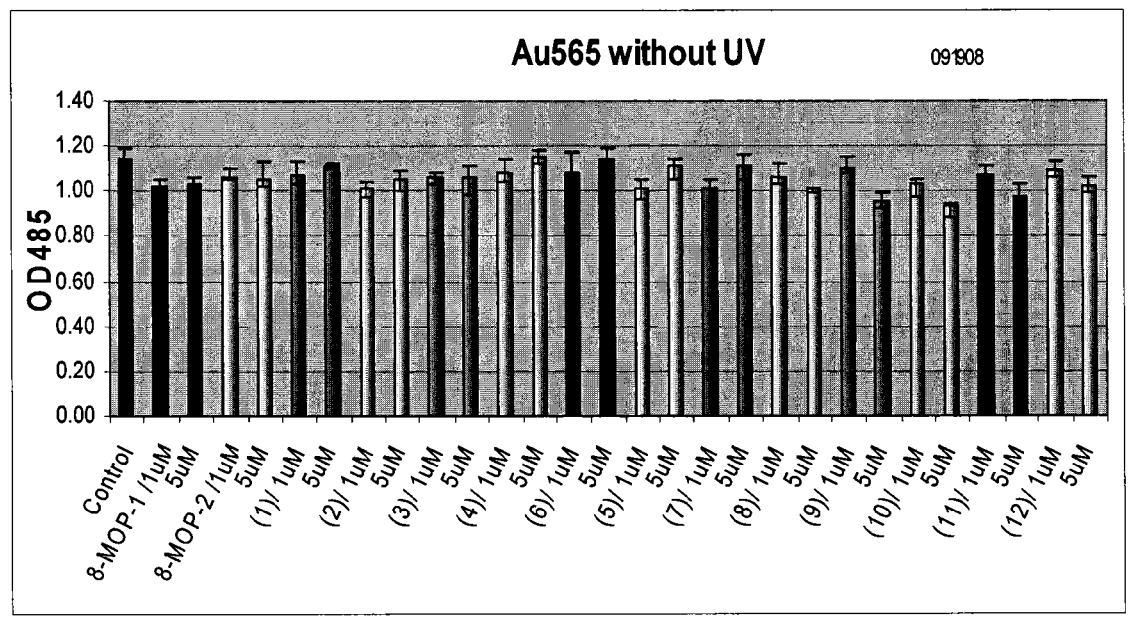
FIG. 5 provides an antenna plot of cell proliferation assay data using various compounds of the present invention with Au565 cancer cells without UV irradiation.
Figure 6:
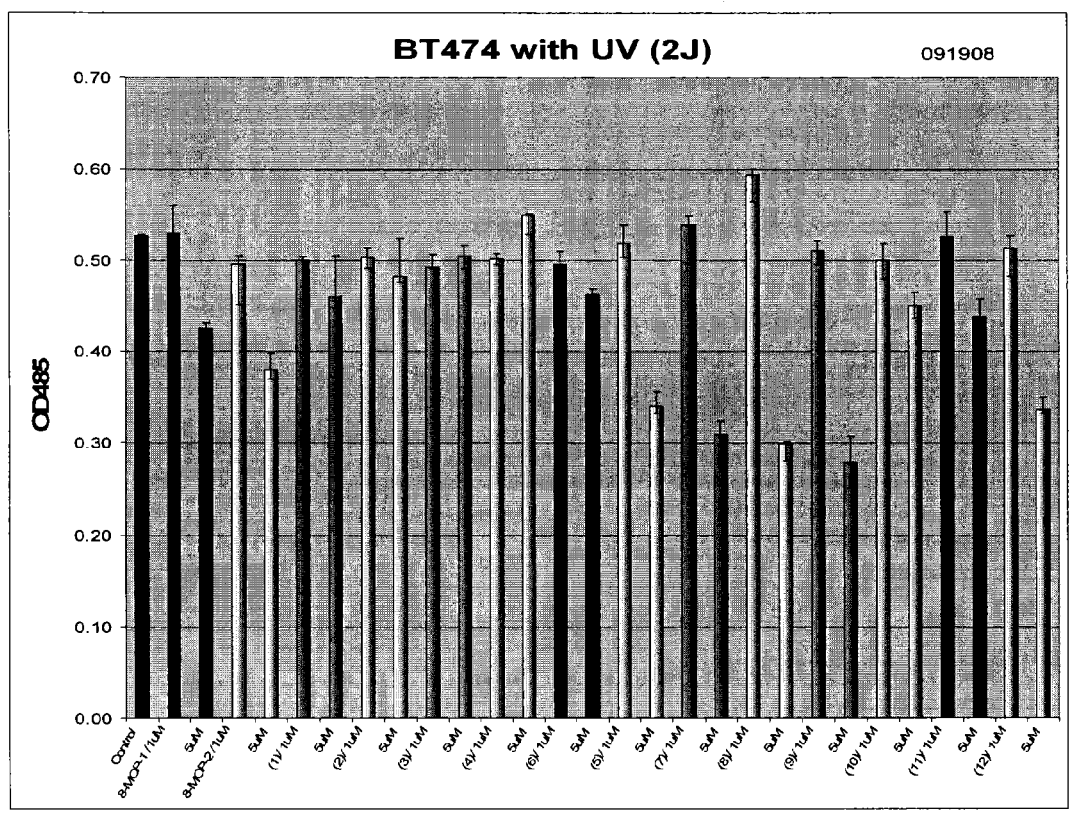
FIG. 6 provides an antenna plot of cell proliferation assay data using various compounds of the present invention with BT474 cancer cells and UV irradiation.
Figure 7:
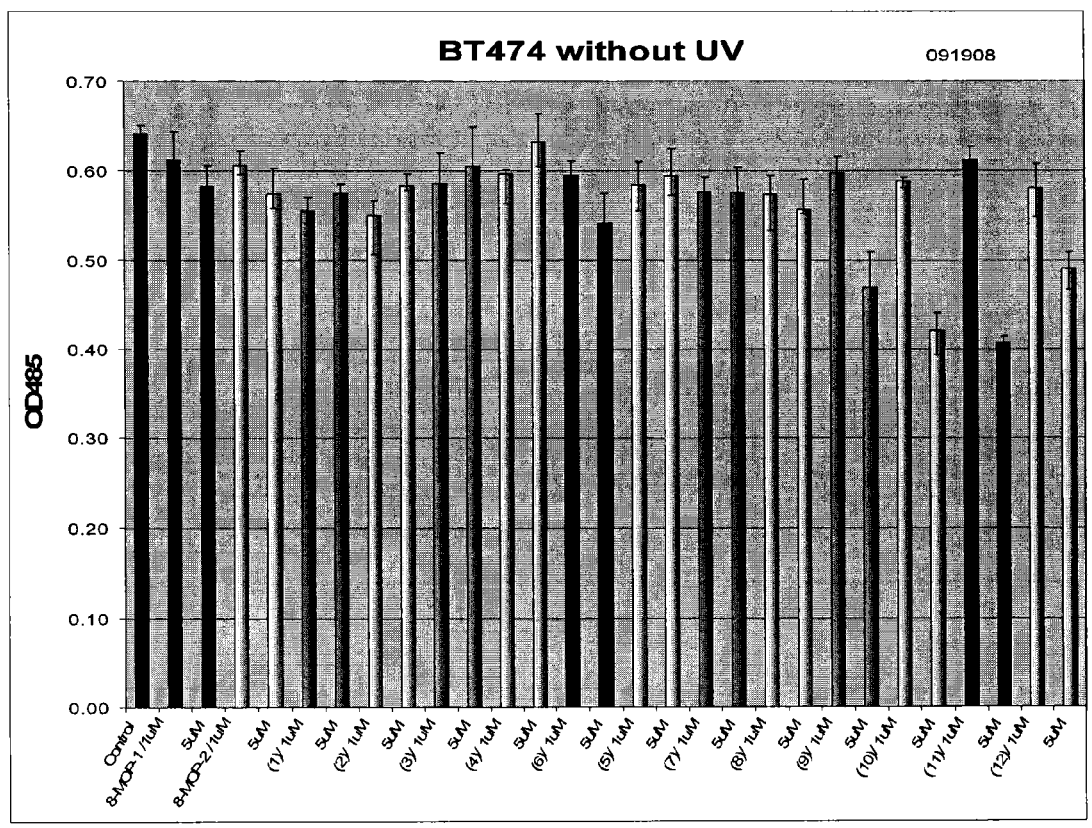
FIG. 7 provides an antenna plot of cell proliferation assay data using various compounds of the present invention with BT474 cancer cells without UV irradiation.
Figure 8:
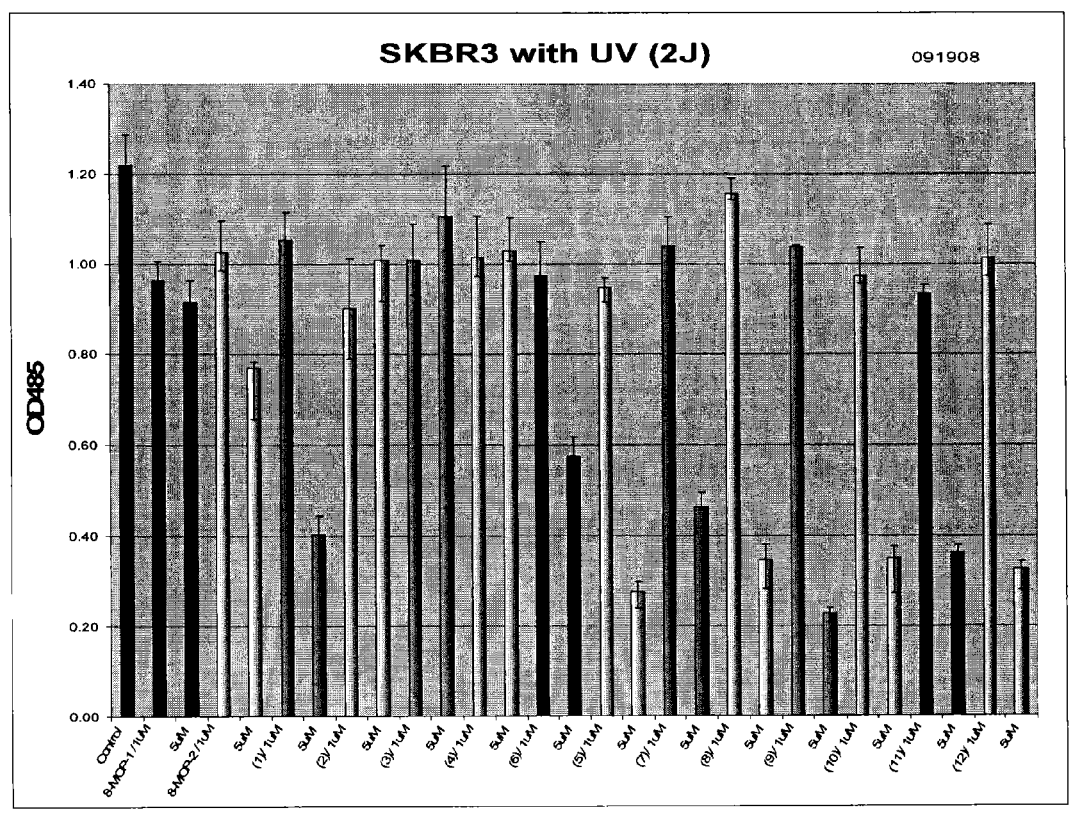
FIG. 8 provides an antenna plot of cell proliferation assay data using various compounds of the present invention with SKBR3 cancer cells and UV irradiation.
Figure 9:
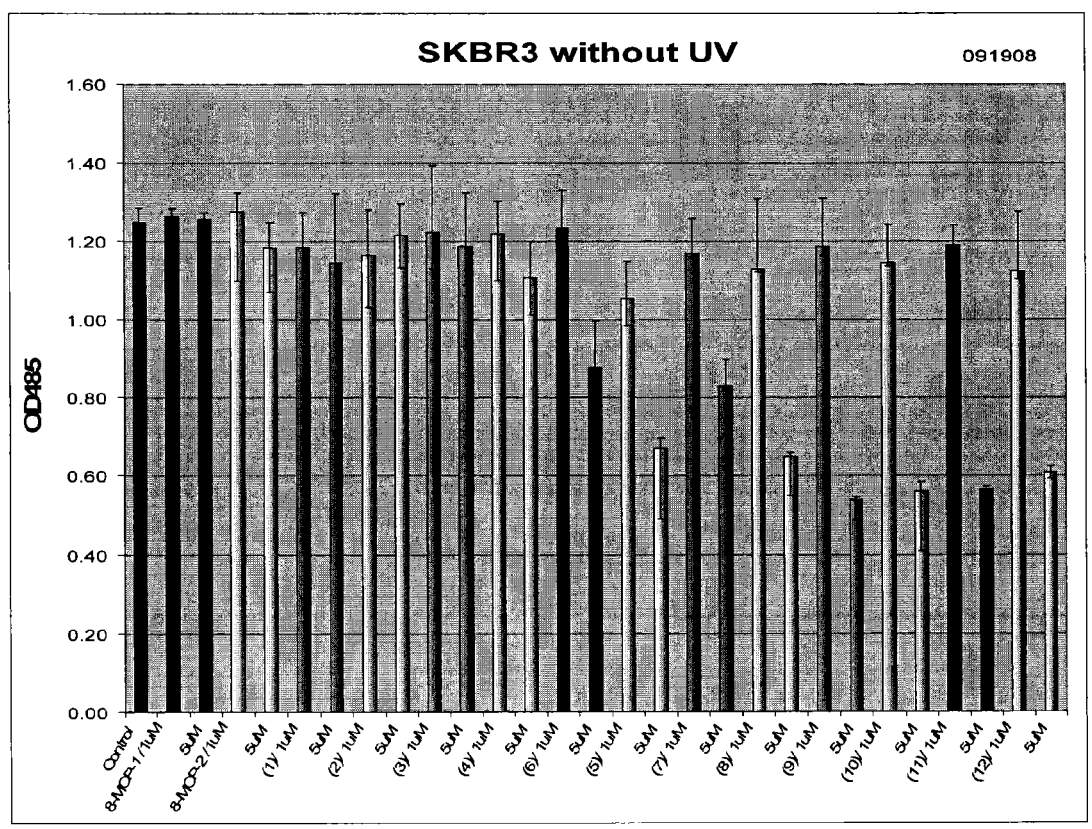
FIG. 9 provides an antenna plot of cell proliferation assay data using various compounds of the present invention with SKBR3 cancer cells without UV irradiation.
Figure 10:
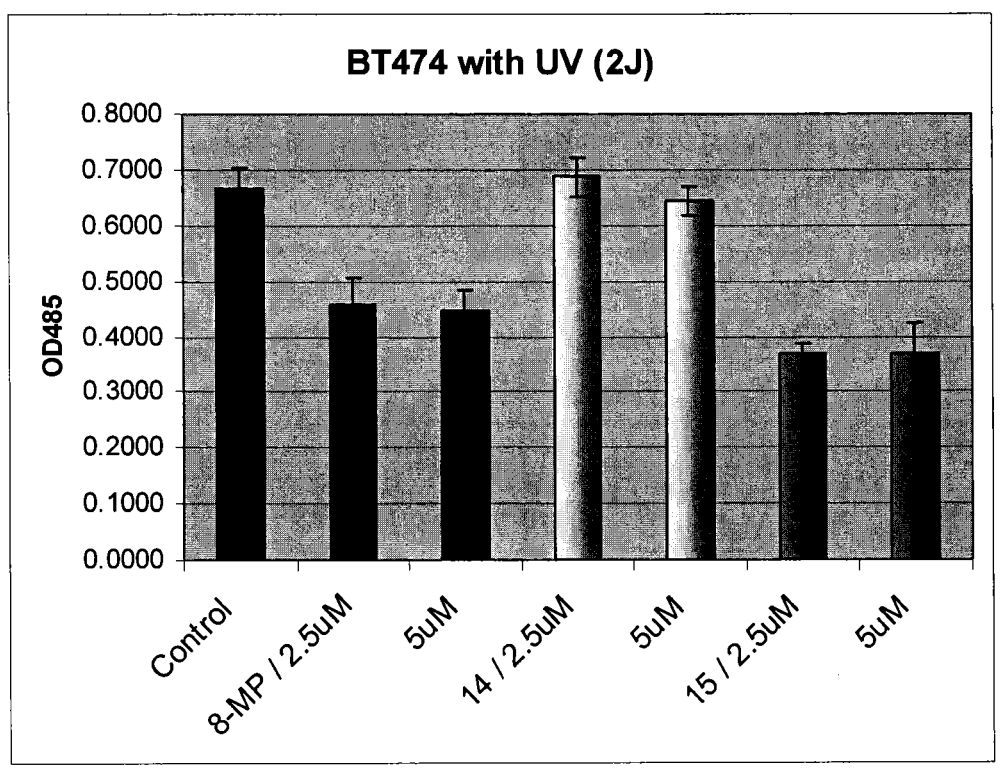
FIG. 10 provides an antenna plot of cell proliferation assay data using compounds 14 and 15 of the present invention with BT474 cancer cells with UV radiation.
Figure 11:
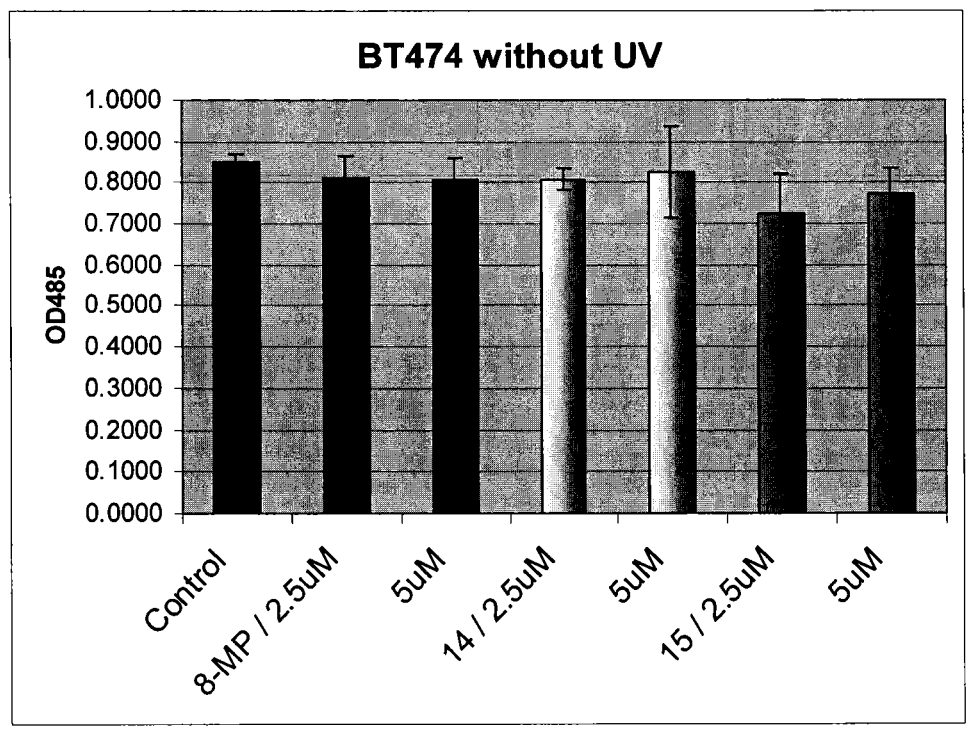
FIG. 11 provides an antenna plot of cell proliferation assay data using compounds 14 and 15 of the present invention with BT474 cancer cells without UV radiation.
Figure 12:
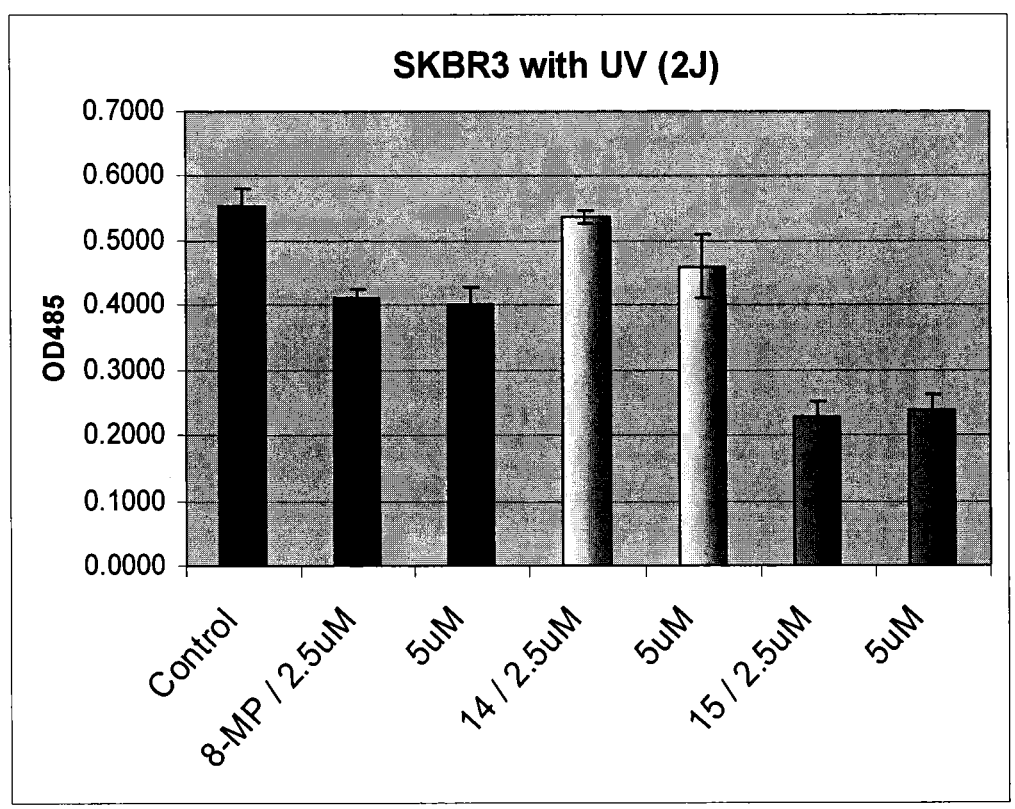
FIG. 12 provides an antenna plot of cell proliferation assay data using compounds 14 and 15 of the present invention with SKBR3 cancer cells with UV radiation.
Figure 13:
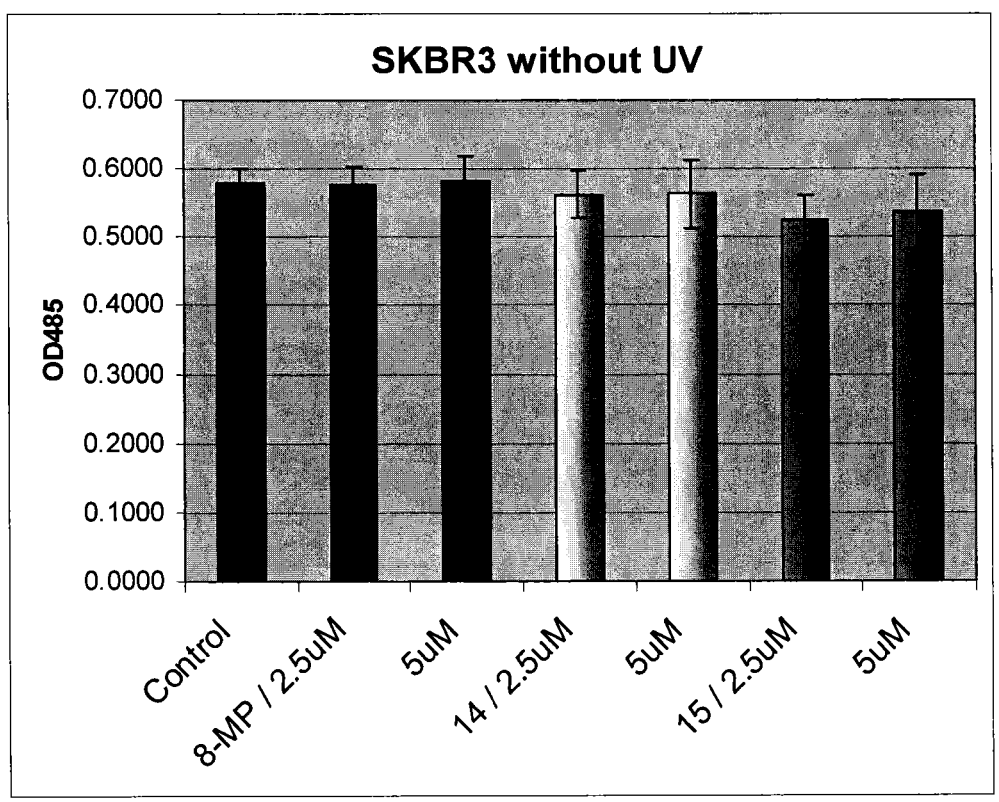
FIG. 13 provides an antenna plot of cell proliferation assay data using compounds 14 and 15 of the present invention with SKBR3 cancer cells without UV radiation.
Figure 14:
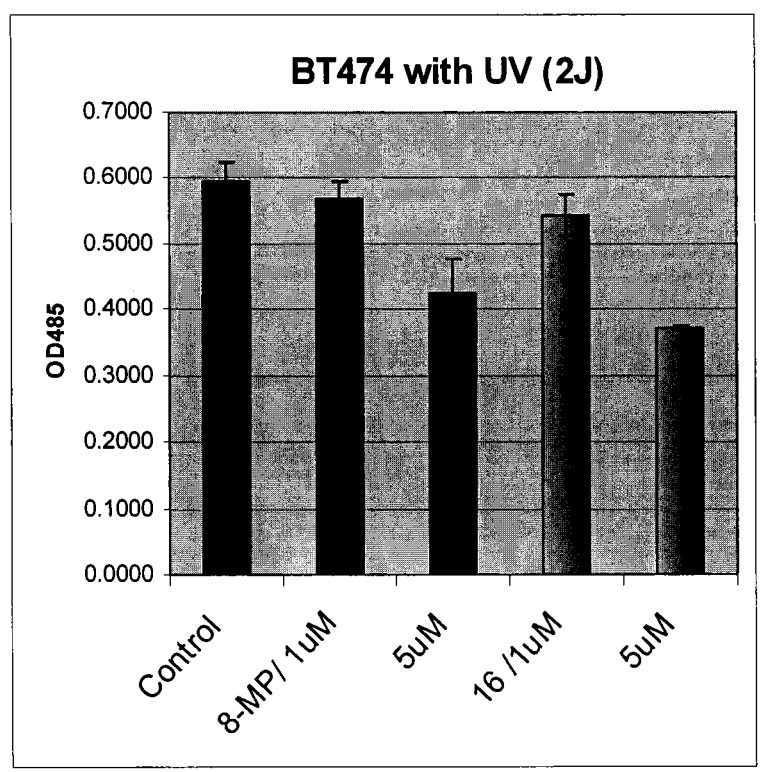
FIG. 14 provides an antenna plot of cell proliferation assay data using compound 16 of the present invention with BT474 cancer cells with UV radiation.
Figure 15:
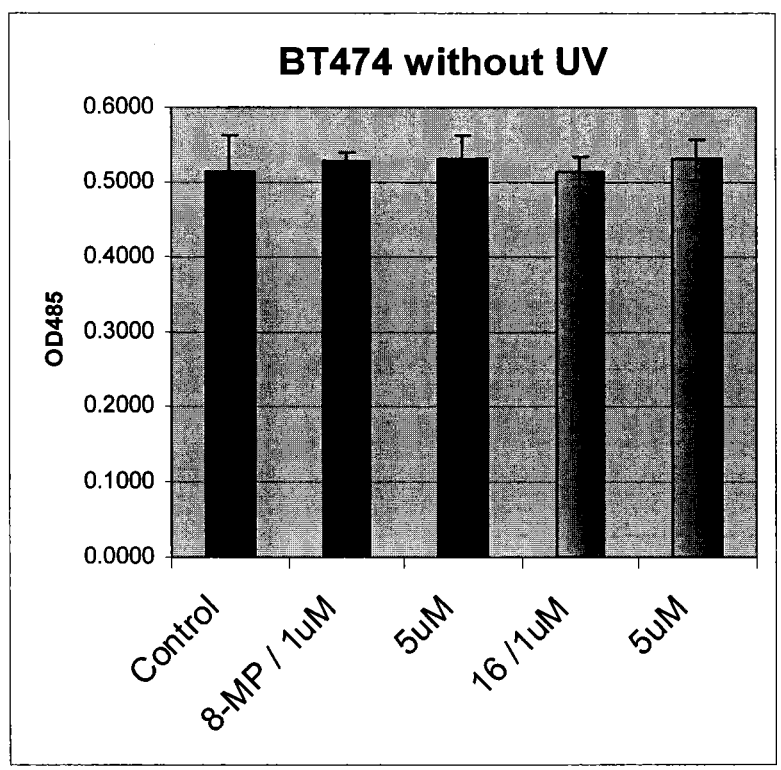
FIG. 15 provides an antenna plot of cell proliferation assay data using compound 16 of the present invention with BT474 cancer cells without UV radiation.
Figure 16:
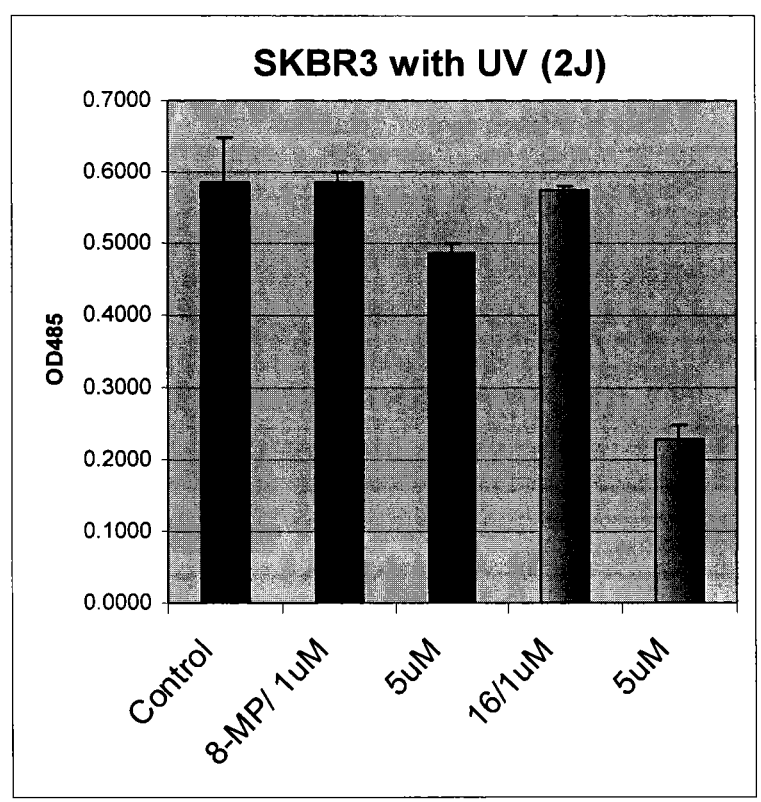
FIG. 16 provides an antenna plot of cell proliferation assay data using compound 16 of the present invention with SKBR3 cancer cells with UV radiation.
Figure 17:
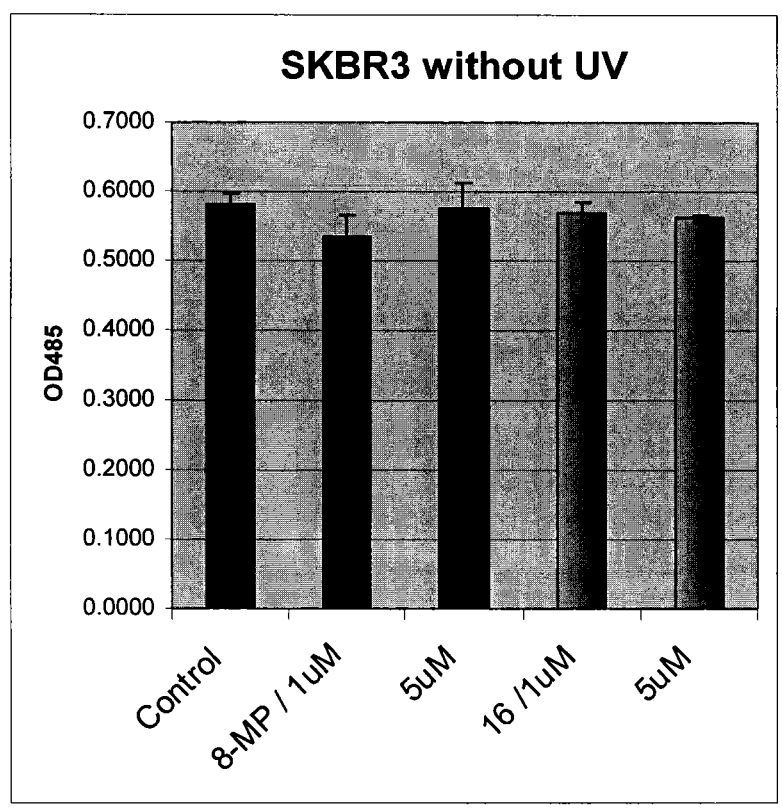
FIG. 17 provides an antenna plot of cell proliferation assay data using compound 16 of the present invention with SKBR3 cancer cells without UV radiation.

FIG. 3 illustrates a system according to one exemplary embodiment of the present invention. Referring to FIG. 3, an exemplary system according to one embodiment of the present invention may have an initiation energy source 1 directed at the subject 4. An activatable pharmaceutical agent 2 and an energy modulation agent 3 are administered to the subject 4. The initiation energy source may additionally be controlled by a computer system 5 that is capable of directing the delivery of the initiation energy.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.).

In other embodiments, endoscopic or laproscopic devices equipped with appropriate initiation energy emitter may be used as the initiation energy source. In such systems, the initiation energy may be navigated and positioned at the pre-selected coordinate to deliver the desired amount of initiation energy to the site.

In further embodiments, dose calculation and robotic manipulation devices may also be included in the system.

The reagents and chemicals useful for methods and systems of the present invention may be packaged in kits to facilitate application of the present invention. In one exemplary embodiment, a kit including a psoralen derivative of Formula (I), and fractionating containers for easy fractionation and isolation of autovaccines is contemplated. A further embodiment of kit would comprise at least one psoralen derivative of Formula (I), at least one energy modulation agent capable of activating the at least one psoralen derivative when energized, and containers suitable for storing the agents in stable form, and preferably further comprising instructions for administering the at least one psoralen derivative and at least one energy modulation agent to a subject, and for applying an initiation energy from an initiation energy source to activate the psoralen derivative. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

Having generally described this invention, a further understanding can be obtained by reference to certain specific examples which are provided herein for purposes of illustration only and are not intended to be limiting unless otherwise specified.

EXAMPLES

Compounds used in the present invention were synthesized in accordance with the following examples:

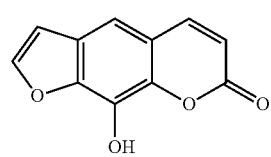 [SMILES: O=c1ccc2cc3ccoc3c(O)c2o1]

8-Hydroxypsoralen synthesized as previously described in Row, E. C.; Brown, S. A.; Stachulski, A. V.; Lennard, M. S. *Bioorg. Med. Chem.* 2006, 14, 3865-3871.

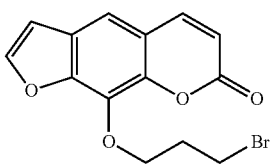 [SMILES: O=c1ccc2cc3ccoc3c(OCCCBr)c2o1]

8-(3-Bromopropyloxy)-psoralen synthesized as previously described in Lartillot, V.; Risler, A.; Andriamialisoa, Z.; Giraud, M.; Sa e Melo, T.; Michel, L.; Santus, R. *Photochemistry and Photobiology* 2003, 78, 623-632.

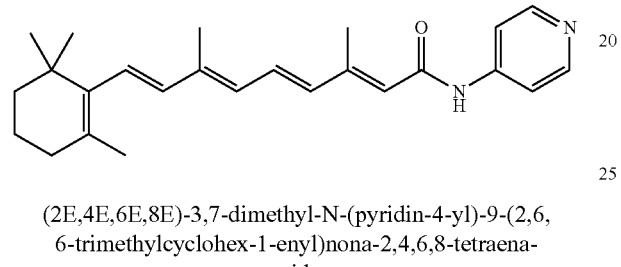

(2E,4E,6E,8E)-3,7-dimethyl-N-(pyridin-4-yl)-9-(2,6,6-trimethylcyclohex-1-enyl)nona-2,4,6,8-tetraenamide synthesized as previously described in Lartillot et al (supra).

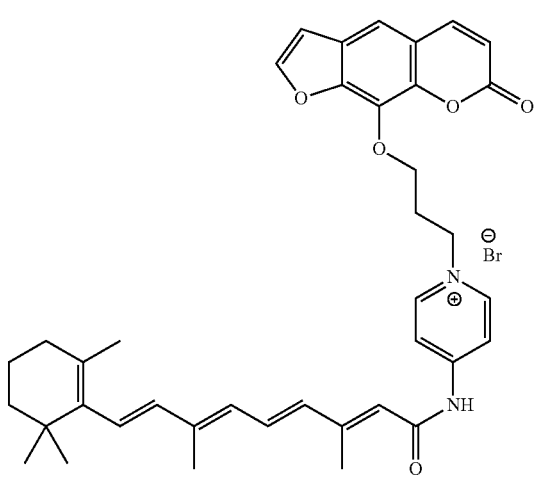

Preparation of Compound 1. Compound 1 was synthesized as previously described in Lartillot et al (supra).

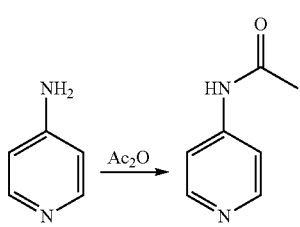

Acetic anhydride (1.75 mL, 18.5 mmol) was added in one portion to 4-aminopyridine (1.74 g, 18.5 mmol). The mixture was heated to 100° C. (bath temperature) for 1 h, cooled to room temperature and concentrated to dryness under reduced pressure. The resulting solid was suspended in saturated aqueous $NaHCO_3$ (40 mL). The mixture was stirred for 10 minutes then insolubles were removed by vacuum filtration. The filter cake was washed with $H_2O$ (20 mL) and dried in vacuo to yield the desired product as a white solid (2.33 g, 93%). $^1H$ NMR ($CD_3OD$, 300 MHz): δ 8.32 (d, 2H, J=4.8 Hz), 7.58 (d, 2H, J=4.8 Hz), 2.12 (s, 3H). EIMS m/z: 137 ([M+H]$^+$).

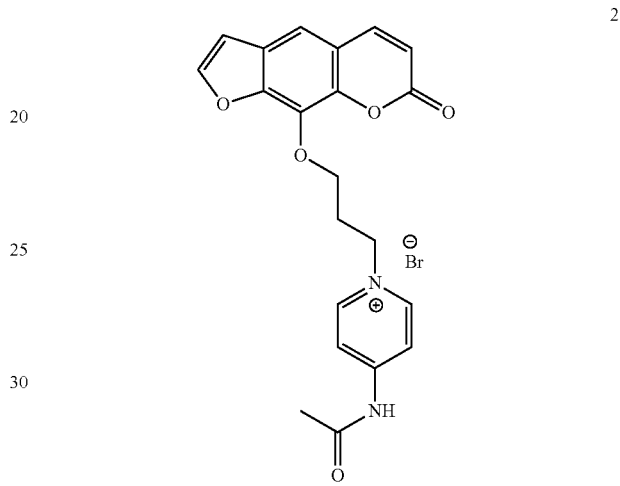

Preparation of Compound 2. Reaction of N-(pyridin-4-yl)acetamide (0.179 g, 1.31 mmol) with 8-(3-bromopropyloxy)-psoralen (0.424 g, 1.31 mmol) in anhydrous acetonitrile (3 mL) was conducted as described for the preparation of 1 to obtain compound 2 as a pale, yellow solid (0.300 g, 50%). EIMS m/z: 379 ([M-Br]$^+$).

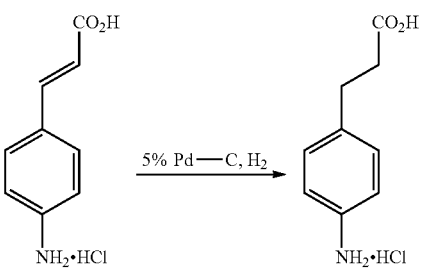

4-aminocinnamic acid hydrochloride (2.0 g, 10 mmol) was hydrogenated at atmospheric pressure in methanol (100 mL) in the presence of 5% Pd—C (250 mg). After the completion of reaction, the reaction mixture was filtered through a Celite pad and washed with methanol. The filtrate was concentrated in vacuo to obtain 4-aminophenylpropionic acid as hydrochloride salt (2.1 g, 100%). EIMS m/z: 166 ([M+1]$^+$).

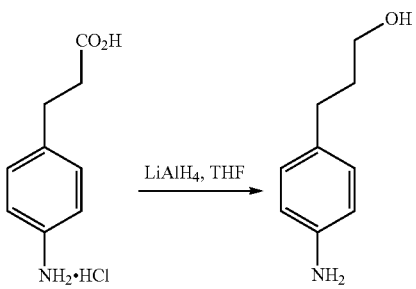

The hydrochloride salt (1.2 g, 6 mmol), obtained as above, was suspended in anhydrous THF (12 mL) and treated with DIEA (2.2 mL; 12 mmol). The resulting mixture was then stirred at room temperature for 2 h and cooled to 0° C. (bath temperature). Solid lithium aluminum hydride (683 mg, 18 mmol) was added in portions. After the addition was complete, the reaction mixture was allowed warm up to room temperature and heated to reflux for 2 h. The reaction mixture was then cooled to room temperature and saturated aqueous $Na_2SO_4$ was added dropwise, with vigorous stirring until no more hydrogen gas was evolved. The precipitate formed was filtered off and the solid was washed with EtOAc. The filtrate was the concentrated in vacuo to yield (4-amino)phenylpropanol as brown oil (455 mg; 50%). EIMS m/z: 152 ([M+1]$^+$).

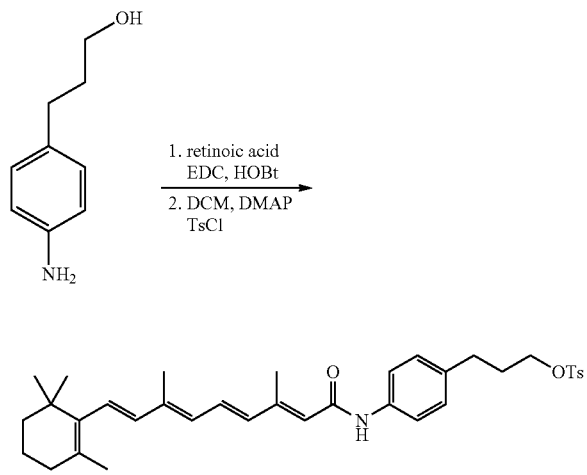

Coupling of (4-amino)phenylpropanol (453 mg; 3 mmol) and retinoic acid (600 mg, 2 mmol) in anhydrous DMF (4 mL) using standard EDC/HOBt coupling condtions yielded the desired amide as a pale, yellow solid (600 mg, 69%). EIMS m/z: 434 ([M+1]$^+$). The amide (510 mg, 1.2 mmol) was dissolved in $CH_2Cl_2$ (4 mL) and added with triethylamine (276 □L, 2 mmol) and DMAP (10 mg). The reaction mixture was then treated with p-toluenesulfonyl chloride (324 mg, 1.7 mmol) and stirred at room temperature overnight. The reaction mixture was then diluted with $CH_2Cl_2$ (10 mL) and washed with water (2×10 mL) and brine (10 mL). The organic layer was dried over $Na_2SO_4$. The solvent was removed in vacuo to afford tosylate which was used without further purification.

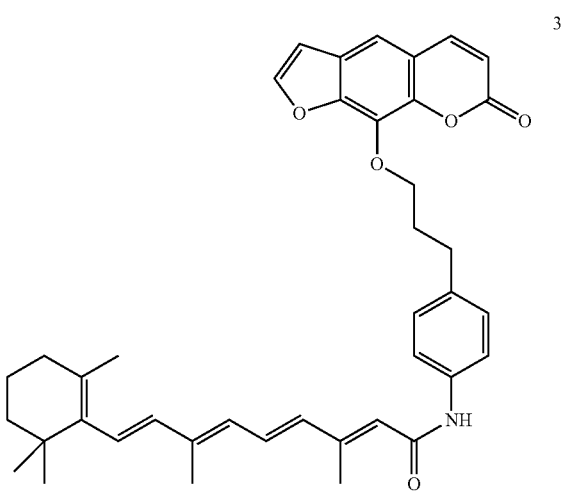 [SMILES: CC1=C(/C=C/C(C)=C/C=C/C(C)=C/C(=O)Nc2ccc(CCCOc3c4occc4cc4ccc(=O)oc34)cc2)C(C)(C)CCC1]

Preparation of Compound 3. (A Comparative Example) To a solution of the aforementioned tosylate (90 mg, 0.15 mmol) in anhydrous DMF (1 mL) 8-hydroxypsoralen (26 mg, 0.13 mmol) and $K_2CO_3$ (35 mg, 0.25 mmol) were added. The reaction mixture was heated at 120° C. for 4 h. Then volatiles were removed in vacuo and the residue obtained was partioned between EtOAc and water. The organic layer was washed with brine and dried over $Na_2SO_4$. The solvent was removed in vacuo and the residue obtained was purified on silica gel column chromatography to afford compound 3 as pale yellow solid (40 mg, 45%). EIMS m/z: 618 ([M+1]$^+$).

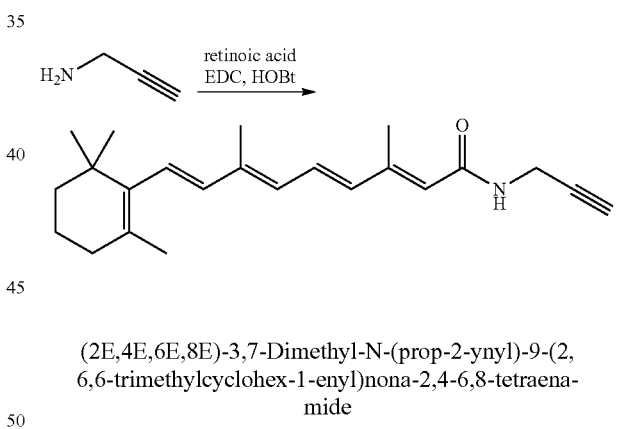

(2E,4E,6E,8E)-3,7-Dimethyl-N-(prop-2-ynyl)-9-(2,6,6-trimethylcyclohex-1-enyl)nona-2,4-6,8-tetraenamide A mixture of retinoic acid (0.60 g, 2.0 mmol), propargylamine (0.11 g, 0.13 mL, 2.0 mmol), EDCI (0.38 g, 2.0 mmol), HOBt-$H_2O$ (0.27 g, 2.0 mmol), $Et_3N$ (0.20 g, 0.28 mL, 2.0 mmol), in anhydrous $CH_2Cl_2$ (30 mL) was stirred at room temperature for 24 h. The reaction mixture was washed with saturated aq. $NaHCO_3$ (50 mL) and water (50 mL). The organic extract was dried, filtered, and concentrated to give a yellow solid (0.57 g, 85%). EIMS m/z: 338 ([M+H]$^+$).

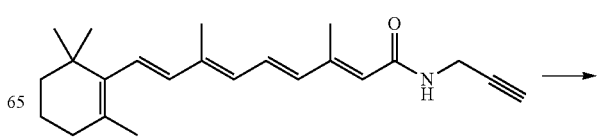

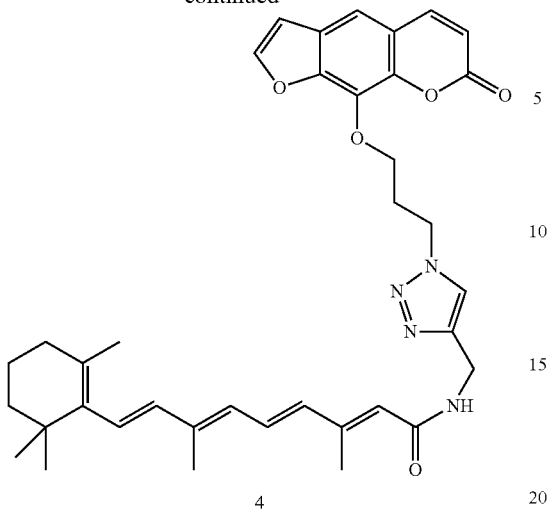

4

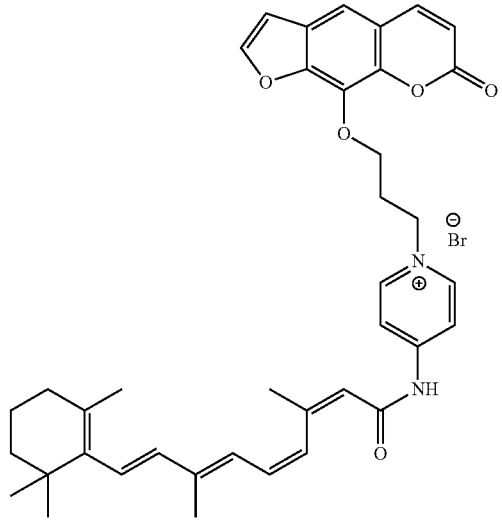

5

Preparation of Compound 4. (A Comparative Example) Copper (50 mg) and 1 M aq. CuSO$_4$ (0.20 mL) were added to a suspension of alkyne (0.35 g, 1.1 mmol), 3-bromopropyloxypsoralen (0.32 g, 1.0 mmol), NaN$_3$ (68 mg, 1.1 mmol), water (1.5 mL), and tert-BuOH (1.5 mL) in a 10 mL microwave reaction vessel. The mixture was irradiated for 10 minutes at 125° C. (100 W) and cooled. The resulting suspension was diluted with water (20 mL) and the precipitate was collected by filtration. The precipitate was washed with water, 0.25 M aq. HCl (20 mL), and petroleum ether (50 mL) The precipitate was then dissolved in chloroform, filtered, concentrated, and purified by silica gel flash column chromatography. EIMS m/z: 645 ([M+Na]$^+$).

Preparation of Compound 5. Reaction of (2Z,4E,6E,8E)-3,7-dimethyl-N-(pyridin-4-yl)-9-(2,6,6-trimethylcyclohex-1-enyl)nona-2,4,6,8-tetraenamide (0.07 g, 0.19 mmol) with 8-(3-bromopropyloxy)-psoralen (0.06 g, 0.19 mmol) in anhydrous acetonitrile (1 mL) was conducted as described for the preparation of 1 to obtain compound 5 as an orange solid (0.03 g, 25%). EIMS m/z 619 ([M−Br]$^+$).

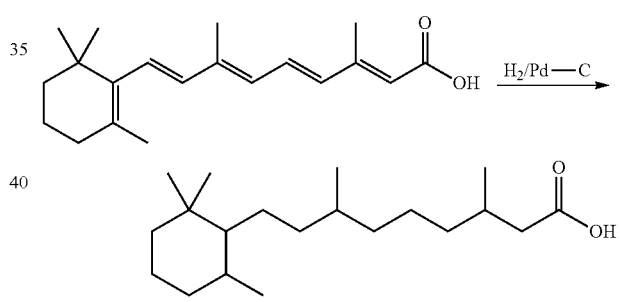

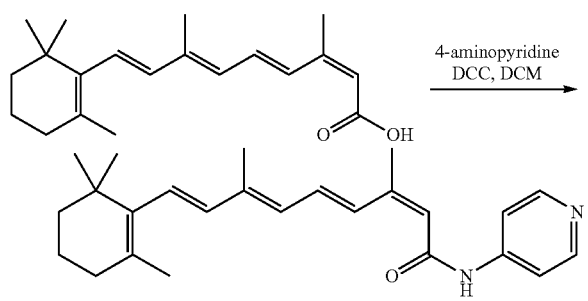

General Amide Coupling Procedure Using DCC.

(2Z,4E,6E,8E)-3,7-Dimethyl-N-(pyridin-4-yl)-9-(2,6,6-trimethylcyclohex-1-enyl)nona-2,4,6,8-tetraenamide A suspension of 13-cis-retinoic acid (0.10 g, 0.33 mmol), CH$_2$Cl$_2$ (5 mL), 4-aminopyridine (0.03 g, 0.33 mmol), and DCC (0.07 g, 0.33 mmol) was stirred at room temperature for 24 h. The mixture was filtered, concentrated, and purified by silica gel flash column chromatography to give the product as a yellow solid (0.07 g, 57%). EIMS m/z: 377 ([M]$^+$), 375 ([M]$^-$).

A suspension of retinoic acid (0.81 g, 2.7 mmol), and 10% palladium on carbon (120 mg) in anhydrous methanol (20 mL) was stirred under an atmosphere of H$_2$ (balloon, 1 atm) for 20 h. The reaction mixture was filtered through a a pad of Celite. The filtrate was concentrated under reduced pressure to give the reduced retinoic acid as a translucent pale oil (0.83 g, 99%). EIMS m/z: 309 ([M−H]$^-$).

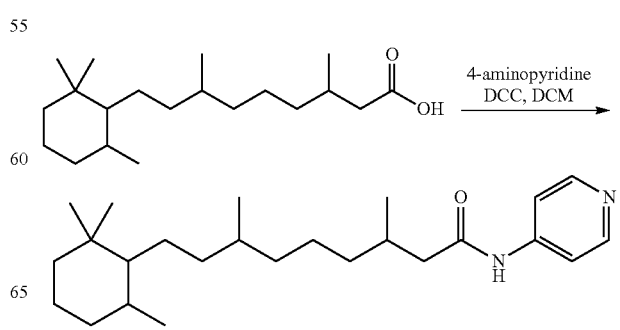

Reaction of the reduced retinoic acid (0.83 g, 2.7 mmol) with 4-aminopyridine (0.26 g, 2.7 mmol) was conducted according to the general amide coupling procedure using DCC to obtain the product as a clear yellow oil (0.88 g, 85%). EIMS m/z: 387 ([M+H]$^+$).

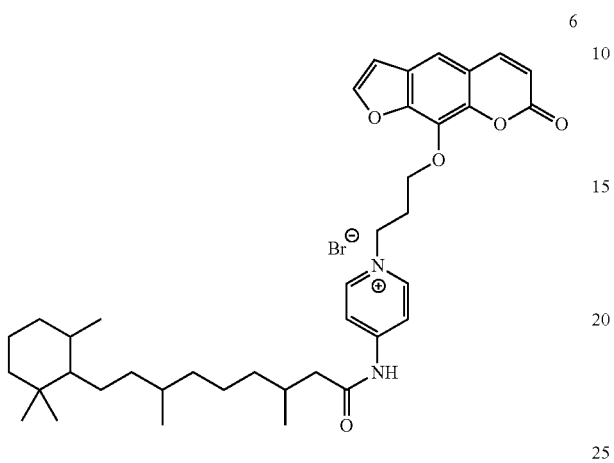

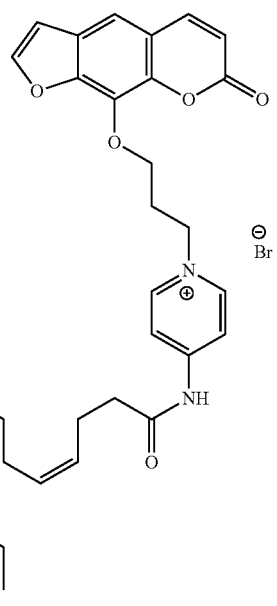

Preparation of Compound 6. Reaction of reduced retinoic acid amide (0.870 g, 2.25 mmol) with 8-(3-bromopropyloxy)-psoralen (0.729 g, 2.25 mmol) in anhydrous acetonitrile (3 mL) was conducted as described for the preparation of 1 to obtain compound 6 as a pale, yellow solid (1.25 g, 78%). EIMS m/z: 629 ([M-Br]$^+$).

Preparation of Compound 7. Reaction of (4Z,7Z,10Z,13Z,16Z,19Z)—N-(pyridin-4-yl)docosa-4,7,10,13,16,19-hexaenamide (0.11 g, 0.28 mmol) with 8-(3-bromopropyloxy)-psoralen (0.09 g, 0.28 mmol) in anhydrous acetonitrile (5 mL) was conducted as described for the preparation of 1 to obtain compound 7 as a yellow/orange solid (0.13 g, 64%). EIMS m/z: 647 ([M-Br]$^+$).

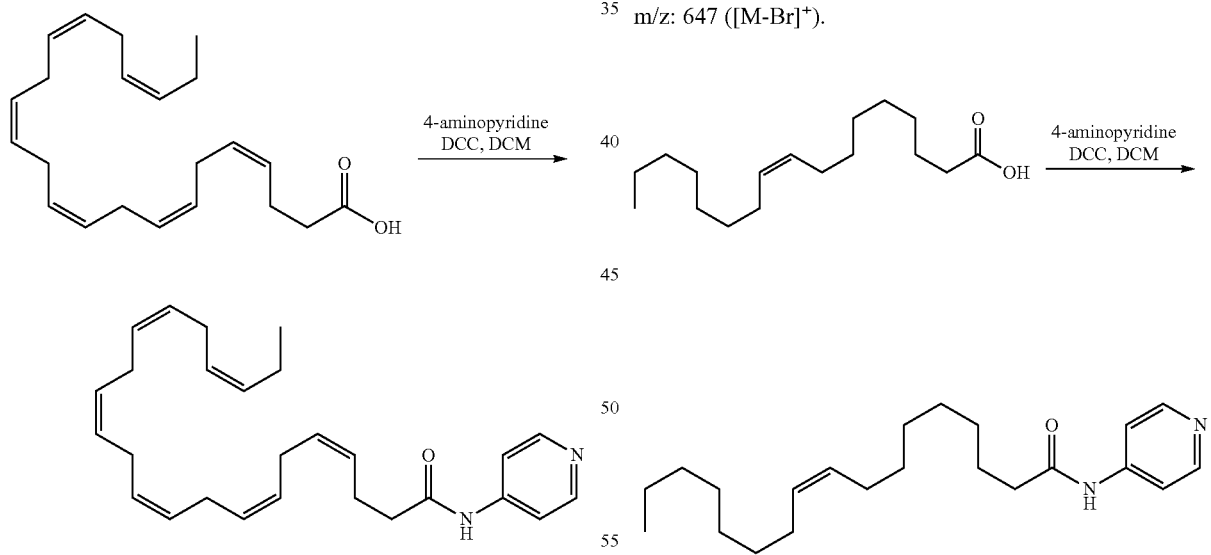

(4Z,7Z,10Z,13Z,16Z,19Z)—N-(Pyridin-4-yl)docosa-4,7,10,13,16,19-hexaenamide

N-(Pyridin-4-yl)-oleamide

Reaction of docosahexaenoic acid (0.10 g, 0.30 mmol) with 4-aminopyridine (0.03 g, 0.30 mmol) was conducted according to the general amide coupling procedure using DCC to obtain the product as a yellow solid (0.11 g, 91%). EIMS m/z: 405 ([M]$^+$).

Reaction of oleic acid (1.00 g, 3.54 mmol) with 4-aminopyridine (0.33 g, 3.54 mmol) was conducted according to the general amide coupling procedure using DCC to obtain the product as a colorless liquid (0.91 g, 72%). EIMS m/z: 359 ([M]$^+$).

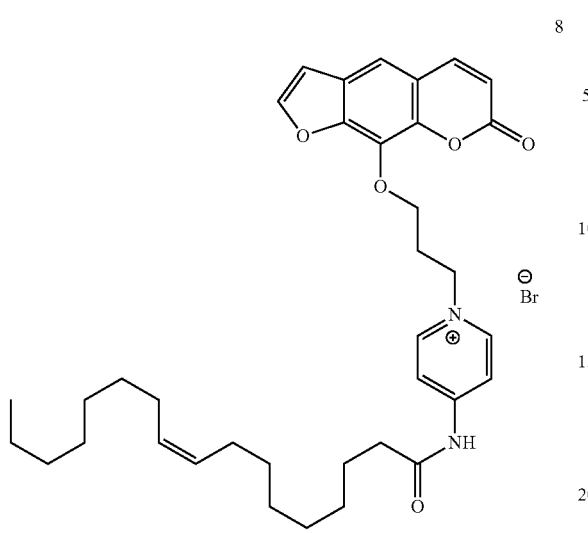

8

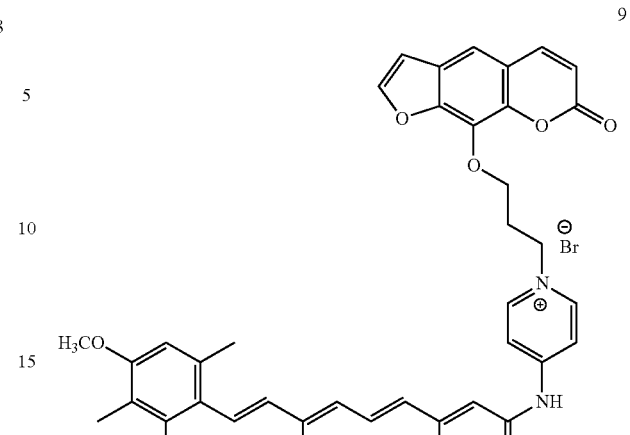

9

Preparation of Compound 8. Reaction of N-(pyridin-4-yl)-oleamide (0.36 g, 1.00 mmol) with 8-(3-bromopropyloxy)-psoralen (0.32 g, 1.00 mmol) in anhydrous acetonitrile (3 mL) was conducted as described for the preparation of 1 to obtain compound 8 as a grey solid (0.34 g, 50%). EIMS m/z: 601 ([M-Br]$^+$).

Preparation of Compound 9. Reaction of (2E,4E,6E,8E)-9-(4-methoxy-2,3,6-trimethylphenyl)-3,7-dimethyl-N-(pyridin-4-yl)nona-2,4,6,8-tetraenamide (0.08 g, 0.19 mmol) with 8-(3-bromopropyloxy)-psoralen (0.06 g, 0.19 mmol) in anhydrous acetonitrile (1 mL) was conducted as described for the preparation of 1 to obtain compound 9 as an orange solid (0.08 g, 61%). EIMS m/z: 645 ([M-Br]$^+$).

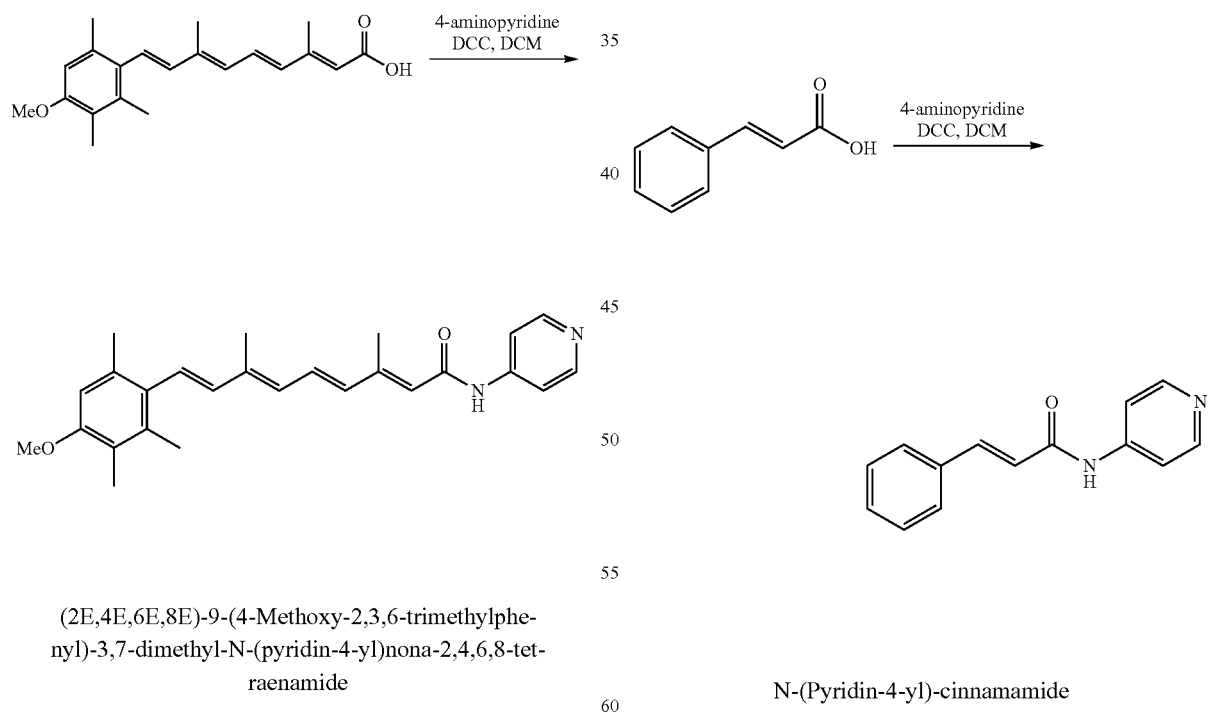

(2E,4E,6E,8E)-9-(4-Methoxy-2,3,6-trimethylphenyl)-3,7-dimethyl-N-(pyridin-4-yl)nona-2,4,6,8-tetraenamide N-(Pyridin-4-yl)-cinnamamide Reaction of acitretin (0.10 g, 0.31 mmol) with 4-aminopyridine (0.03 g, 0.31 mmol) was conducted according to the general amide coupling procedure using DCC to obtain the product as a yellow solid (0.08 g, 61%). EIMS m/z: 403 ([M]$^+$), 401 ([M]$^-$).

Reaction of trans-cinnamic acid (0.74 g, 5.00 mmol) with 4-aminopyridine (0.47 g, 5.00 mmol) was conducted according to the general amide coupling procedure using DCC to obtain the product as a white solid (0.76 g, 68%). EIMS m/z: 225 ([M]$^+$), 223 ([M]$^-$).

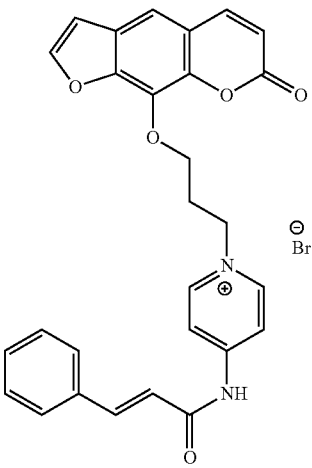

Preparation of Compound 10. Reaction of N-(pyridin-4-yl)-cinnamamide (0.22 g, 1.00 mmol) with 8-(3-bromopropyloxy)-psoralen (0.32 g, 1.00 mmol) in anhydrous acetonitrile (5 mL) was conducted as described for the preparation of 1 to obtain compound 10 as a white solid (0.43 g, 78%). EIMS m/z: 467 ([M-Br]$^+$).

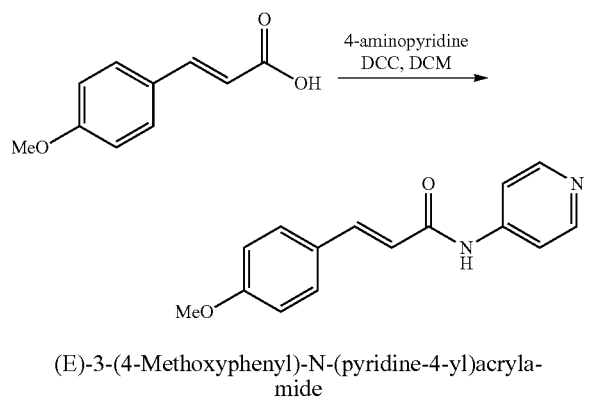

(E)-3-(4-Methoxyphenyl)-N-(pyridine-4-yl)acrylamide

Reaction of 4-methoxycinnamic acid (0.89 g, 5.00 mmol) with 4-aminopyridine (0.47 g, 5.00 mmol) was conducted according to the general amide coupling procedure using DCC to obtain the product as a white solid (0.18 g, 14%). EIMS m/z: 255 ([M]$^+$).

11

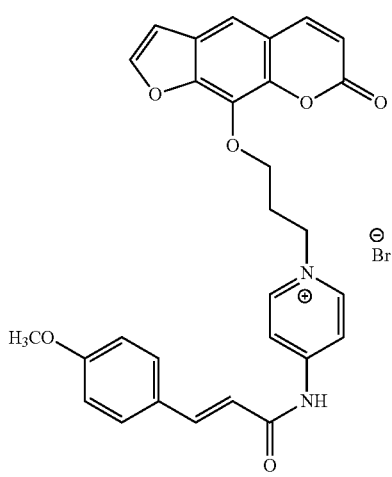

Preparation of Compound 11. Reaction of (E)-3-(4-methoxyphenyl)-N-(pyridin-4-yl)acrylamide (0.18 g, 0.70 mmol) with 8-(3-bromopropyloxy)-psoralen (0.23 g, 0.70 mmol) in anhydrous acetonitrile (10 mL) was conducted as described for the preparation of 1 to obtain compound 11 as a yellow solid (0.10 g, 25%). EIMS m/z: 497 ([M-Br]$^+$).

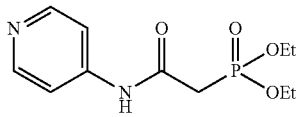 [SMILES: CCOP(=O)(CC(=O)Nc1ccncc1)OCC]

Diethyl 2-oxo-2-(pyridin-4-ylamino)ethylphosphonate

Was synthesized as previously described in Lartillot et al (supra).

(2E,4E)-3-Methyl-5-(2,6,6-trimethylcyclohex-1-enyl)penta-2,4-dienenitrile synthesized as previously described in Valla, A.; Valla, B.; Le Guillou, R.; Cartier, D.; Dufosse, L.; Labia, R. *Helv. Chim. Acta* 2007, 90, 512-519.

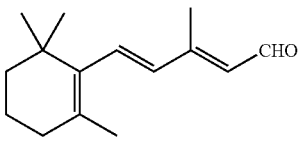 [SMILES: CC1=C(/C=C/C(C)=C/C=O)C(C)(C)CCC1]

(2E,4E)-3-Methyl-5-(2,6,6-trimethylcyclohex-1-enyl)penta-2,4-dienal synthesized as previously described in Valla et al (supra).

(2E,4E,6E)-5-Methyl-N-(pyridin-4-yl)-7-(2,6,6-trimethylcyclohex-1-enyl)hepta-2,4,6-trienamide synthesized as previously described in Lartillot et al (supra).

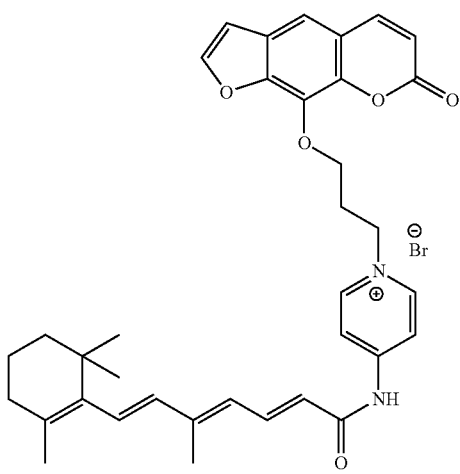

Preparation of Compound 12. Reaction of (2E,4E,6E)-5-methyl-N-(pyridin-4-yl)-7-(2,6,6-trimethylcyclohex-1-enyl)hepta-2,4,6-trienamide (0.34 g, 1.02 mmol) with 8-(3-bromopropyloxy)-psoralen (0.33 g, 1.02 mmol) in anhydrous acetonitrile (10 mL) was conducted as described for the preparation of 1 to obtain compound 12 as a yellow/orange solid (0.43 g, 64%). EIMS m/z: 579 ([M-Br]+).

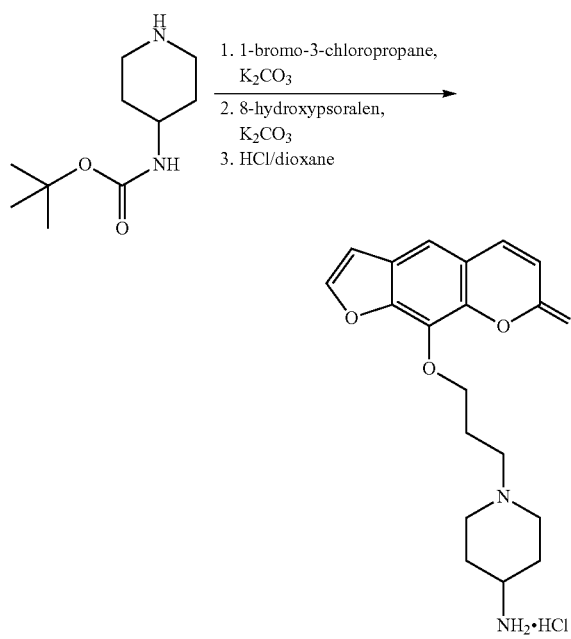

To a solution of tert-butyl 4-piperidinylcarbamate (800 mg, 4 mmol) in anhydrous acetonitrile (8 mL), was added 1-bromo-3-chloropropane (693 mg, 4.4 mmol) and anhydrous K₂CO₃ (690 mg, 5 mmol). The reaction mixture was heated at 70° C. for 3 h. The contents were then cooled to room temperature and added with a solution of 8-hydroxypsoralen (808 mg, 4 mmol) in anhydrous DMF (6 mL) followed by solid K₂CO₃ (690 mg, 5 mmol). The reaction mixture was heated at 90° C. for 5 h. The contents were then cooled to room temperature and partitioned between ethyl acetate (20 mL) and water (20 mL). The aqueous layer was extracted with ethyl acetate (20 mL) and the combined organics were then washed with water (30 mL) and brine (20 mL) and dried over anhydrous Na₂SO₄. The solvent was removed in vacuo and the residue obtained was purified on silica gel column chromatography using methanol/CH₂Cl₂ as eluant to afford the desired product as a dark brown solid (790 mg, 45%).

The aforementioned product (760 mg, 0.58 mmol) was treated with 4M HCl in dioxane (3 mL) at room temperature. The reaction was stirred overnight and the solvent was removed in vacuo. The residue obtained was washed with ether twice and dried under vacuum to afford the amine hydrochloride as a light brown solid (708 mg, 100%).

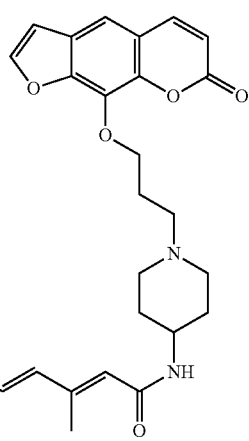

Preparation of Compound 13. Coupling of aforementioned amine hydrochloride (124 mg, 0.3 mmol) and retinoic acid (100 mg, 0.33 mmol) in anhydrous DMF (2 mL) using standard EDC/HOBt coupling condtions yielded 13 as a pale, yellow solid (187 mg, 100%). EIMS m/z: 625 ([M+H]+).

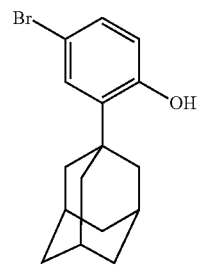 [SMILES: Oc1ccc(Br)cc1C12CC3CC(CC(C3)C1)C2]

2-(1-Adamantyl)-4-bromophenol synthesized as previously described in Liu, Z.; Xiang, J. Org. Process Res. Dev. 2006, 10, 285-288.

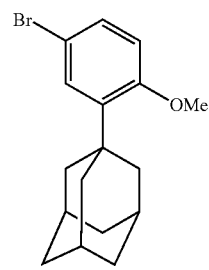

2-(1-Adamantyl)-4-bromoanisole synthesized as previously described in Liu et al (supra).

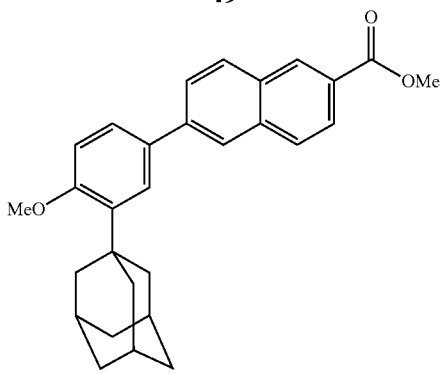

Methyl 6-(3-(1-adamantyl)-4-methoxyphenyl)-2-naphthoate synthesized as previously described in Liu et al (supra).

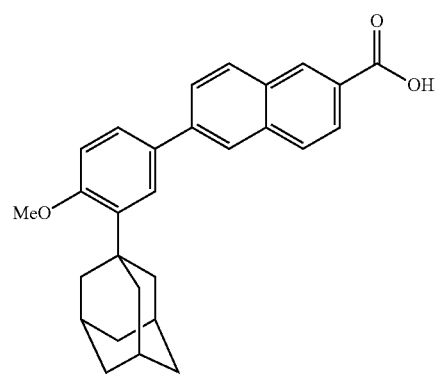 [SMILES: COc1ccc(-c2ccc3cc(C(=O)O)ccc3c2)cc1C12CC3CC(CC(C3)C1)C2]

6-(3-(1-Adamantyl)-4-(methoxyphenyl)-2-naphthoic acid synthesized as previously described in Liu et al (supra).

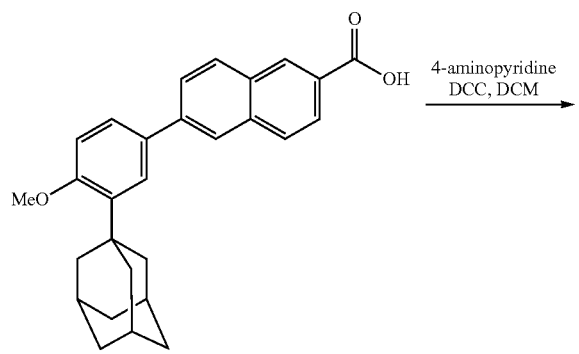

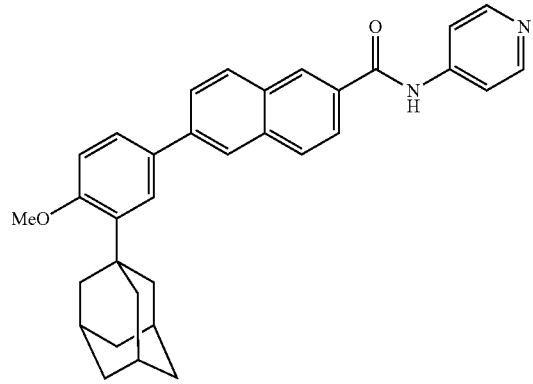

6-(3-(1-Adamantyl)-4-methoxyphenyl)-N-(pyridin-4-yl)-2-naphthamide

Reaction of 6-(3-(1-adamantyl)-4-(methoxyphenyl)-2-naphthoic acid (0.89 g, 2.16 mmol) with 4-aminopyridine (0.20 g, 2.16 mmol) was conducted according to the general amide coupling procedure using DCC to obtain the product as a yellow solid (0.58 g, 54%). $^1$H NMR (CDCl$_3$) δ 8.57 (m, 2H), 8.39 (s, 1H), 8.34 (s, 1H), 8.05-7.82 (m, 5H), 7.70-7.53 (m, 4H), 7.00 (m, 1H), 3.91 (s, 3H), 2.20-2.08 (m, 8H), 1.83-1.75 (m, 7H).

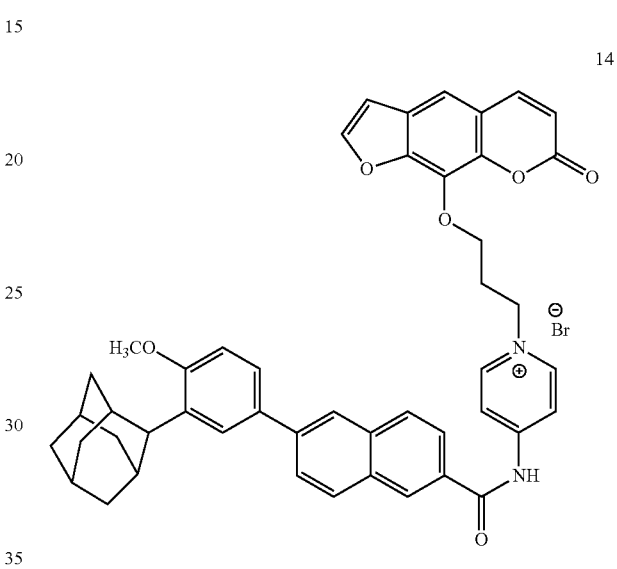

Preparation of Compound 14. Reaction of 6-(3-(1-adamantyl)-4-methoxyphenyl)-N-(pyridin-4-yl)-2-naphthamide (0.49 g, 1.00 mmol) with 8-(3-bromopropyloxy)-psoralen (0.32 g, 1.00 mmol) in anhydrous acetonitrile (10 mL) and N-methylpyrrolidone (6 mL) was conducted as described for the preparation of 1 to obtain compound 14 as a yellow solid (0.45 g, 55%).

EIMS m/z: 731 ([M-Br]$^+$).

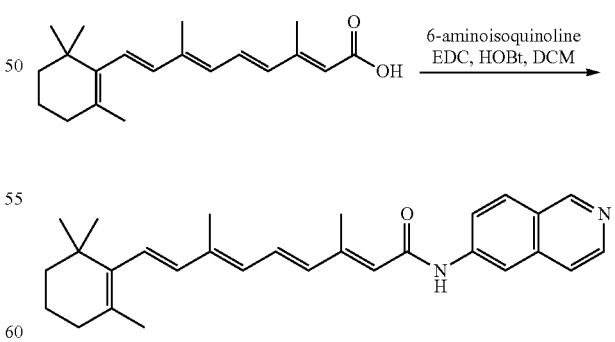

Coupling of 6-aminoisoquinoline (72 mg, 0.5 mmol) and retinoic acid (200 mg, 0.67 mmol) in anhydrous DMF (1 mL) using standard EDC/HOBt coupling condtions yielded the desired amide a pale, yellow solid (300 mg, 90%). EIMS m/z: 427 ([M+1]$^+$)

15

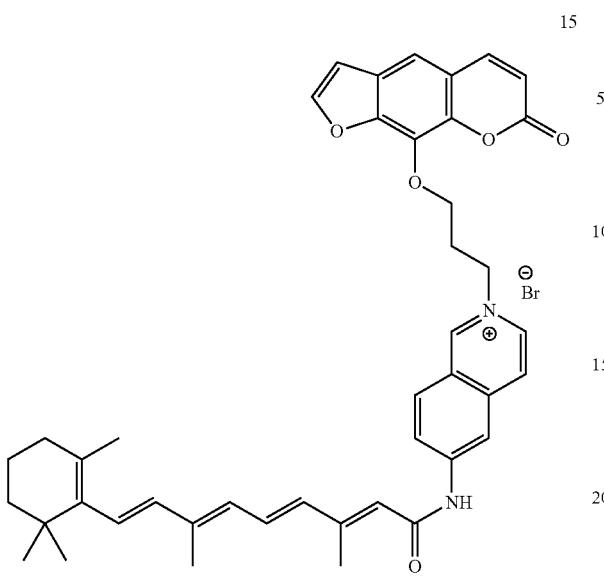

16

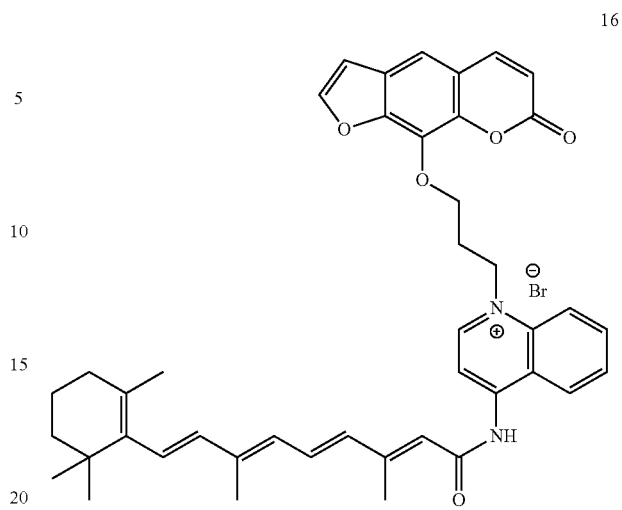

Preparation of Compound 15. Reaction of the aforementioned amide (110 mg, 0.26 mmol) with 8-(3-bromopropyloxy)-psoralen (84 mg, 0.26 mmol) in anhydrous acetonitrile (3 mL) and DMF (0.5 mL) was conducted as described for the preparation of 1 to obtain compound 15 as a brick red solid (77 mg, 40%). EIMS m/z: 670 ([M-Bi]$^+$).

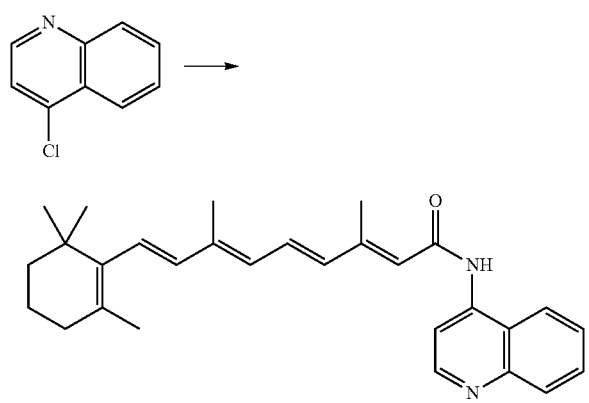

A mixture of 4-chloroquinoline (486 mg, 3 mmol), acetamide (2.13 g, 36 mmol) and $K_2CO_3$ (2.9 g, 21 mmol) was thoroughly vortexed on a mixer and subjected to microwave irradiation at 175° C. for 1 h. The reaction mixture was cooled to room temperature and partitioned between EtOAc and water. The aqueous layer was extracted with EtOAc and the combined organic extracts were washed with water and brine and dried over anhydrous $Na_2SO_4$. The solvent was removed in vacuo to yield 4-aminoquinoline as a brown solid (260 mg, 60%). EIMS m/z: 145 ([M+1]$^+$).

Coupling of 4-aminoquinoline (144 mg, 1 mmol) and retinoic acid (200 mg, 0.67 mmol) in anhydrous DMF (2 mL) using standard EDC/HOBt coupling conditions yielded the desired amide a pale, yellow solid (70 mg, 25%). EIMS m/z: 427 ([M+1]$^+$).

Preparation of Compound 16. Reaction of the aforementioned amide (70 mg, 0.17 mmol) with 8-(3-bromopropyloxy)-psoralen (55 mg, 0.17 mmol) in anhydrous acetonitrile (3 mL) and DMF (0.5 mL) was conducted as described for the preparation of 1 to obtain compound 16 as a brick red solid (18 mg, 14%). EIMS m/z: 670 ([M-Br]$^+$).

Cell Culture and Proliferation Assay

BT474, Au565, and SKBR3 breast cancer cell lines were obtained from the American Type Culture Collection (Manassas, Va.). Cells were maintained in RPMI 1640 supplemented with 10% fetal bovine serum from GIBCO (Carlsbad, Calif.) in a humidified atmosphere of 5% $CO_2$ at 37° C. The proliferation assay was carried out in 96 well plates in a final volume of 100 ul/well culture medium with Cell Proliferation Reagent WST-1 from Roche Diagnostics (Mannheim, Germany), which is based on a colorimetric assay for the quantification of cell proliferation and cell viability depending on the cleavage of the WST-1 by mitochondrial dehydrogenases in viable cell. For each assay, the cells were pre-treated with psoralen derivatives and psoralen (as a positive control) at the concentration indicated in the figures for four hours to allow compound uptake by the cells, followed by exposing the cells to UV (2 Joules) in UV Stratalinker 1800 from Stratagene (La Jolla, Calif.). After changing the medium to remove non-absorbed compounds, the cells were returned to the incubator for 48 hour continued culture before starting colorimetric reaction by adding 10 ul/well Cell Proliferation Reagent WST-1. When the reaction incubation for two hours at 37° C. in the tissue culture incubator was completed, the reaction samples were ready to be analyzed in the plate reader (TECAN, Australia) at 480 mm.

The test results are shown in FIGS. 4-17. FIGS. 4-9 show the results of the cell proliferation assays for 8-MOP (two samples, 8-MOP-1 and 8-MOP-2) and Compounds 1-12.

FIGS. 10-13 show the results of the cell proliferation assays for 8-MOP and Compounds 14-15. FIGS. 14-17 show the results of the cell proliferation assays for 8-MOP and Compound 16. The cells were pretreated with compounds at the concentrations as indicated in the figures for four hours to allow compound uptake by the cells, followed by exposing the cells to UV in the conditions showed in the figures. The cells without the exposure to UV were used as a control. After changing the medium and an additional incubation for 48 hours, colorimetric reaction was initiated by adding WST-1 and the quantification of cell proliferation and cell viability were based on the cleavage of WST-1. The wavelength for measuring the absorbance of the cleavage products was 485 nm, which correlates with active cells.

Obviously, additional modifications and variations of the present invention are possible in light of the above teachings. It is therefore to be understood that within the scope of the appended claims, the invention may be practiced otherwise than as specifically described herein.

The invention claimed is:
1. A pharmaceutical composition comprising:
one or more psoralen compounds selected from the group of compounds having structures 6-8 and 14:

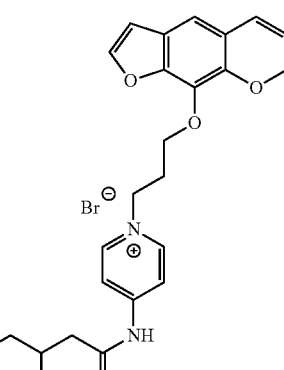

6

7

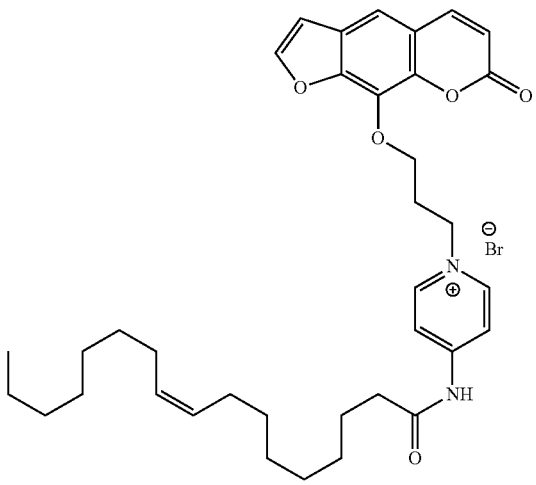

8

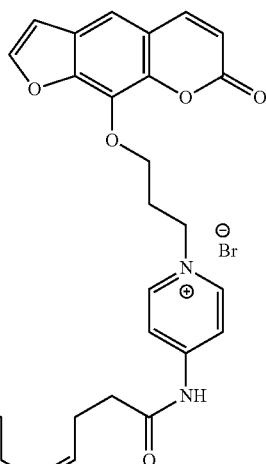

14

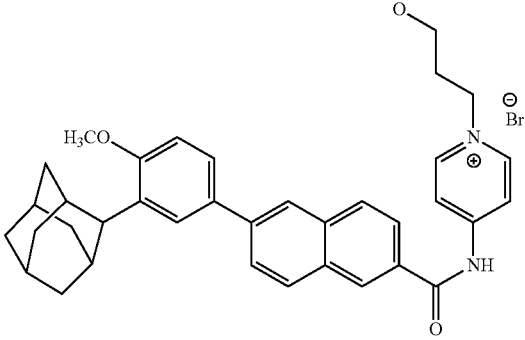

and
a pharmaceutically acceptable carrier.

2. The pharmaceutical composition of claim 1, further comprising one or more energy modulation agents.

3. The pharmaceutical composition of claim 1, further comprising one or more plasmonics-active agents.

4. The pharmaceutical composition of claim 2, further comprising one or more plasmonics-active agents.

5. The pharmaceutical composition of claim 2, wherein the one or more energy modulation agents is at least one member selected from the group consisting of a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence.

6. The pharmaceutical composition of claim 5, further comprising one or more plasmonics-active agents.

7. The pharmaceutical composition of claim 1, further comprising one or more members selected from the group consisting of sterile diluents, antibacterial agents, antioxidants, chelating agents, buffers, and tonicity adjusting agents.

8. The pharmaceutical composition of claim 5, further comprising one or more members selected from the group consisting of sterile diluents, antibacterial agents, antioxidants, chelating agents, buffers, and tonicity adjusting agents.

9. The pharmaceutical composition of claim 6, further comprising one or more members selected from the group consisting of sterile diluents, antibacterial agents, antioxidants, chelating agents, buffers, and tonicity adjusting agents.

* * * * *